United States Patent [19]

Sternberg et al.

[11] Patent Number: 5,378,618
[45] Date of Patent: Jan. 3, 1995

[54] VITRO HEADFUL PACKAGING SYSTEM FOR CLONING DNA FRAGMENTS AS LARGE AS 95KB

[75] Inventors: Nat L. Sternberg, West Chester, Pa.; Brian L. Sauer, Wilmington, Del.

[73] Assignee: E. I. Du Pont de Nemours and Company, Wilmington, Del.

[21] Appl. No.: 954,423

[22] Filed: Sep. 29, 1992

Related U.S. Application Data

[63] Continuation of Ser. No. 397,071, Aug. 22, 1989, abandoned, which is a continuation-in-part of Ser. No. 182,112, Apr. 15, 1988, abandoned.

[51] Int. Cl.$^6$ .................. C12N 15/00; C12N 15/66
[52] U.S. Cl. .................. 435/172.3; 435/320.1; 935/31
[58] Field of Search .................. 435/172.3, 69.1, 320.1, 435/252.3–252.35, 91.1, 91.4, 91.41; 935/29, 31, 72–74

[56] References Cited

FOREIGN PATENT DOCUMENTS 0183571  4/1986  European Pat. Off. .
9102801  7/1991  WIPO .

OTHER PUBLICATIONS

Chem. Abstracts, vol. 106, No. 9, 2 Mar. 1987, Abstract No. 64185d, p. 332.
Chem. Abstracts, vol. 107, No. 2, 20 Jul. 1987, Sternberg et al., Abstract No. 18676n, p. 170.
Chem Abstracts, vol. 93, No. 5, 4 Aug. 1980, Enquist et al., Abstract No. 41298s.
Chem. Abstracts, vol. 88, No. 13, 27 Mar. 1978, Sternberg et al., Abstract No. 85885g, p. 232.
Chem. Abstracts, vol. 87, No. 5, 1 Aug. 1977, No. 35765b, p. 322.
Sternberg et al., J. Mol. Biol., pp. 453–468, vol. 194 (1987).
Sternberg et al., J. Mol. Biol. pp. 469–479, vol. 194 (1987).
Sternberg et al., J. Mol. Biol., pp. 197–212, vol. 187 (1986).
Blumenthal, Focus, 11:31 pp. 41–46 (Summer 1989).
Yarmolinsky & Sternberg, The Bacteriophage, Bacteriaphage P1, Chapter 9, pp. 291–437 (1988).
Abremski et al., Cell, pp. 1301–1311, vol. 32 (Apr. 1983).
Burke et al., Science, pp. 806–812, vol. 236 (May 15, 1987).
Gaitanaies et al., Gene, pp. 1–11, vol. 46 (1986).
Murray, Lambada II, pp. 395–432, Cold Spring Harbor Lab., Cold Spring Harbor, N.Y. (1986).
Rao et al., J. Mol. Biol., pp. 565–578, vol. 185 (1985).
Black, Gene, pp. 97–101, vol. 46 (1986).
Sternberg et al., "Cloning of HMW DNA (50–100 kb) in Bacteriophage Pi Cloning Vectors", Cold Spring Harbor Lab, Apr. 20, 1989.
Sauer et al., Gene, 70:331–341 (1988).
Sternberg et al., J. Mol. Biol., 207:111–133 (1989).

Primary Examiner—James Martinell

[57] ABSTRACT

This relates to an in vitro headful packaging system for cloning foreign DNA fragments as large as 95 kb. Also of concern is a method of cloning and controlling amplification of DNA fragments as large as 95 kb in a vector containing a multicopy replicon under control of a lac promoter as well as vectors useful for cloning foreign fragments of DNA as large as 95 kb and lysogens to prepare pac-cleavage proficient extract and head-tail proficient extract.

30 Claims, 14 Drawing Sheets

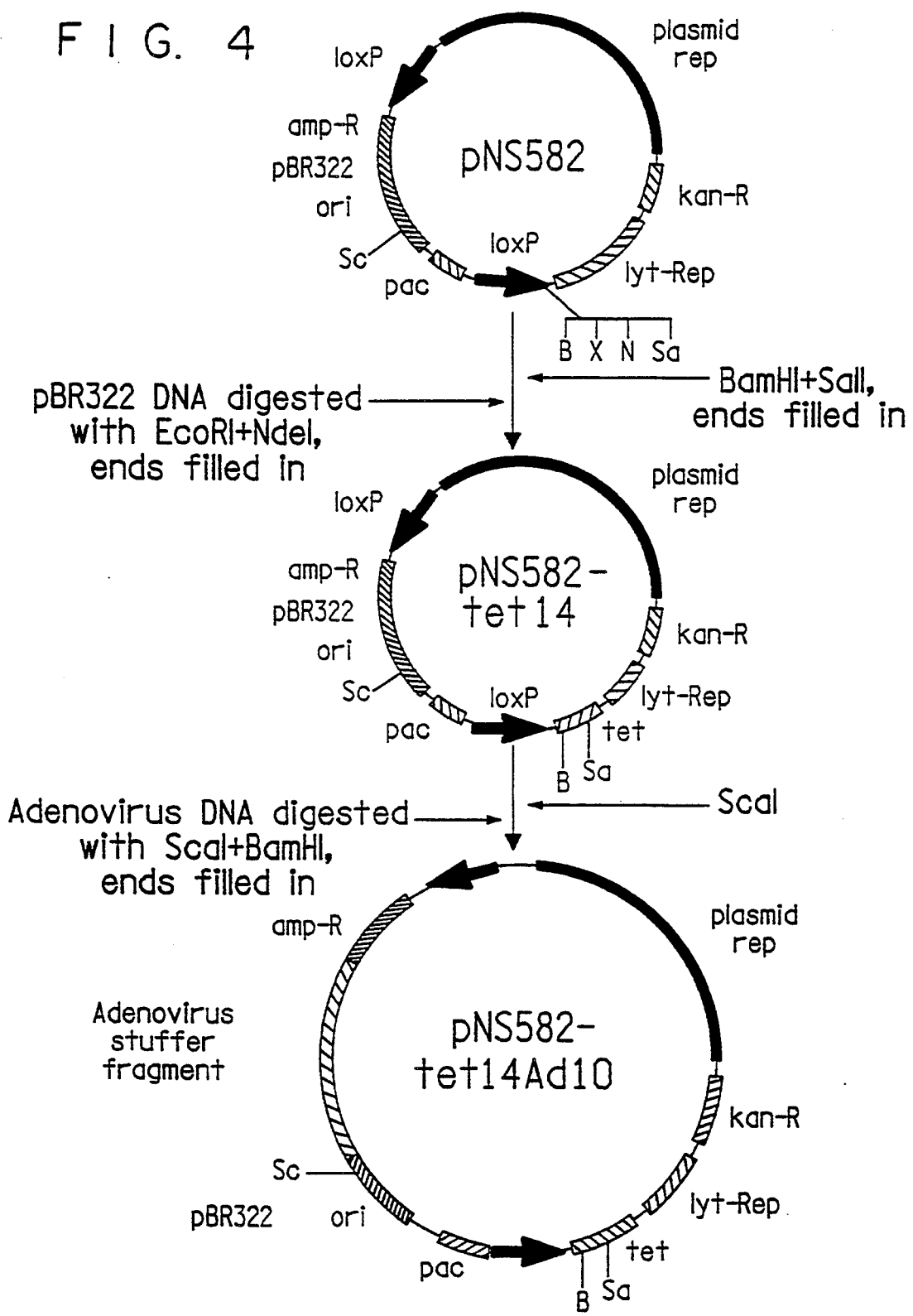

lanes 1. kan-R, amp-R transformants of DH5
2. amp-R transformants of BS591
3. kan-R transformants of BS591
4. kan-R, amp-R transformants of BS591 concentration of IPTG used for culture depicted in each lane (uM)

1) 0
2) 10
3) 20
4) 40
5) 80
6) 200
7) 500
8) 1000

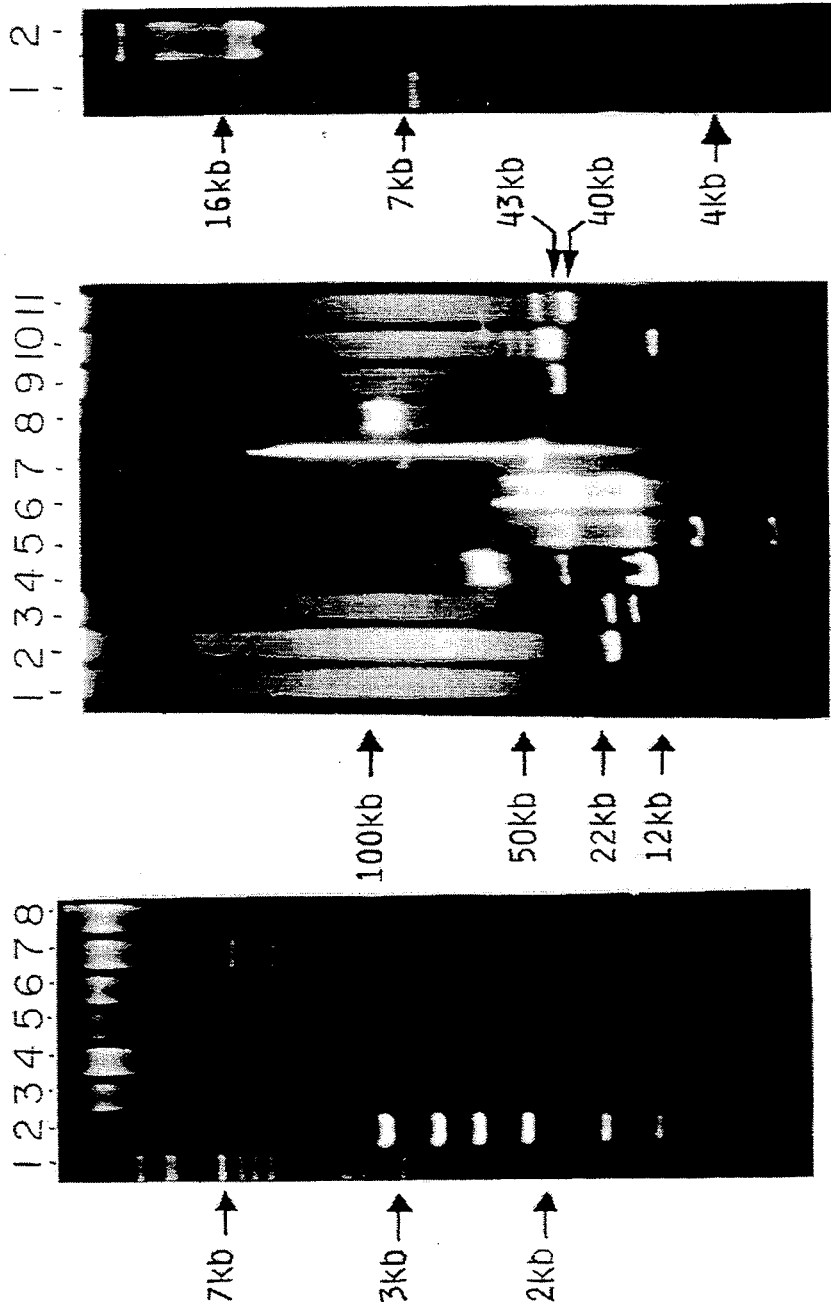

Concatemer of insert and pNS582tet14 vector DNA
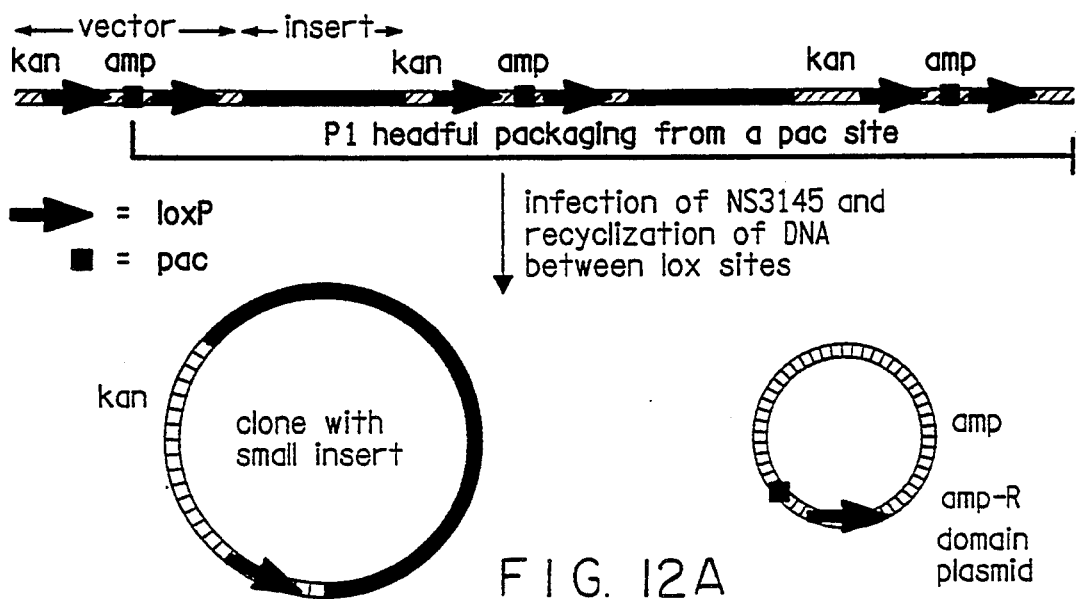
FIG. 12A
FIG. 12B
insert DNA ligated between the two arms of pNS582tet14Ad10 DNA
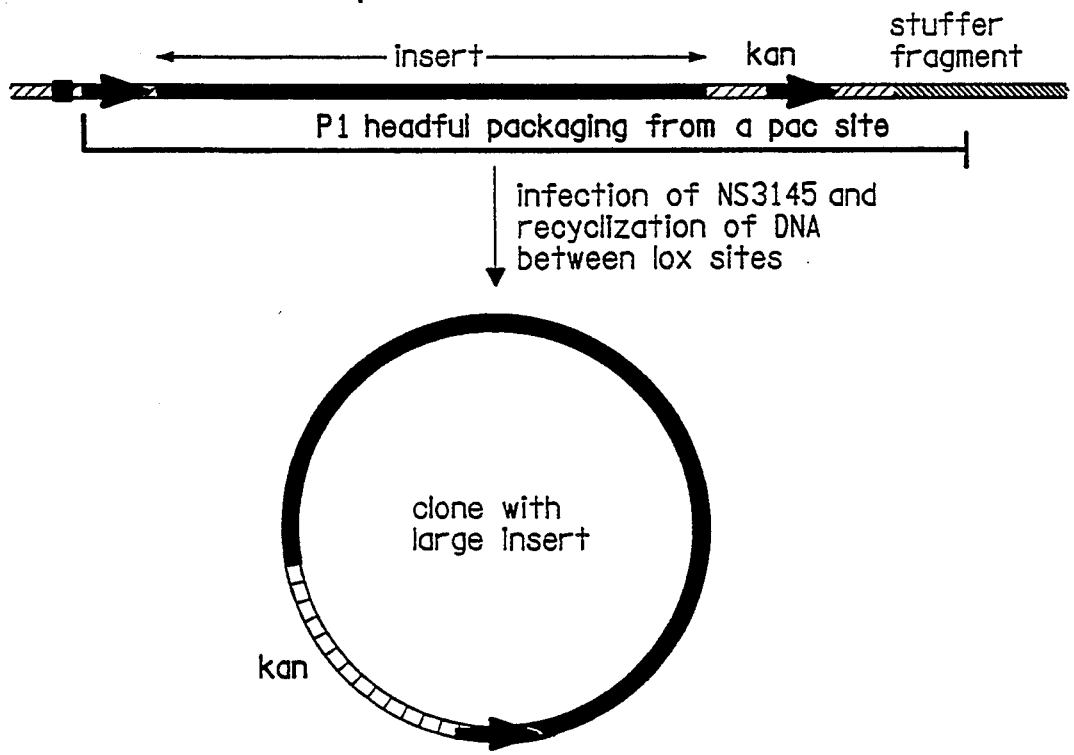

VITRO HEADFUL PACKAGING SYSTEM FOR CLONING DNA FRAGMENTS AS LARGE AS 95KB

GOVERNMENT INTEREST: ACKNOWLEDGMENT

The invention described herein was made during the course of work under Grant No. 1 R01 GM42952-01 awarded by the National Institute of General Medical Sciences and Grant Nos. 8 R01 HG00339-02, 7 R01 HG00339-03 and 5 R01 HG00339-04 awarded by the National Center for Human Genome Research.

CROSS-REFERENCE TO RELATED APPLICATION

This is a continuation of application Ser. No. 07/397,071 filed Aug. 22, 1989, now abandoned, which is a continuation-in-part of U.S. Ser. No. 07/182,112, filed Apr. 15, 1988, abandoned.

FIELD OF THE INVENTION

This invention relates to a system for cloning DNA fragments and, more particularly, to an in vitro headful packaging system for cloning DNA fragments as large as 95 kb. Amplification of cloned DNA can also be controlled.

BACKGROUND OF THE INVENTION

Recombinant DNA technology has made it possible to clone and amplify DNA fragments from the chromosomes of high eucaryotes (plants and animals) using vectors that can be propagated in bacteria such as *Escherichia coli* (*E. coli*).

If DNA is to be introduced directly into bacteria that have been made competent for that uptake, then the DNA must be relatively small (less than 20 kb) since the efficiency of DNA uptake into cells decreases dramatically as the size of the DNA increase above 20 kb. Accordingly, alternate delivery routes have been sought in order to introduce large DNA into bacteria. The technique of packaging bacteriophage vector DNA into virus particles was developed to meet this need. It has the advantage of delivering the packaged DNA to cells by infection with near unit efficiency. Bruning et al., Gene 4, 85-107 (1978) and Collins et al., Proc. Natl. Acad. Sci., 75, 4242-4246 (1978) took advantage of the in vitro packaging reaction of bacteriophage lambda, developed by Sternberg et al., Gene 1, 255-280 (1975) to package large inserts cloned into cosmid vectors which are fusions of a plasmid and a bacteriophage lambda cos site. The cos site provides the recognition element needed to initiate the packaging of DNA into a lambda bacteriophage head.

The major disadvantage of the lambda bacteriophage in vitro packaging reaction is that the lambda bacteriophage head cannot accommodate more than 49.5 kb of DNA. Thus, taking into account that the cos vector itself is about 2 kb in size, then no more than 47 kb of clonable DNA can be inserted into the vector and packaged into a lambda bacteriophage head. (Murray, Lambda II 236, 395-432, Cold Spring Harbor Laboratory, Cold Spring Harbor, N.Y. 1986).

Accordingly, the lambda phage cannot be used to clone genes bigger than 50 kb, and mapping chromosomal segments of DNA that are several megabases in size by "walking" or "jumping" protocols is difficult, given the limitations of the lambda bacteriophage system. Researchers have explored two systems as potential tools for cloning larger DNA fragments: phage systems with head sizes larger than bacteriophage lambda and yeast cloning vectors.

Rao et al., J. Mol. Biol. 185, 565-578 (1985), demonstrated that T4 DNA (about 165 kilobases) could be packaged into bacteriophage T4 heads in vitro. The efficiency of that reaction is $10^4$-$10^5$ plaque-forming units (PFU) per microgram of added T4 DNA. However, Black, Gene 46, 97-101 (1986), showed that efforts to package vector DNA of various sorts into T4 heads and recover that DNA following injection into appropriate bacteria was no more efficient than $10^2$-$10^3$ PFU per microgram of added DNA. Black's result suggests that it may be very difficult to use the T4 packaging system to generate a complete library of 150 kb inserts of a complex genome such as that of mammalian cells (i.e., the equivalent of about 20,000 inserts of 150 kb). A second, and perhaps more difficult problem, is the absence of a cloning vector that can take advantage of the T4 packaging capability to clone and amplify large DNA fragments. Indeed, since very little is known about the T4 sequences that are needed to initiate T4 packaging, it may be difficult to construct such a vector.

Burke et al., Science 236, 806-812 (1987), were able to clone large segments of mammalian DNA as minichromosomes in yeast. The DNA to be inserted is cloned into a vector containing a yeast replicating element, a yeast partitioning element or centromere, and yeast telomeres and the resulting chimeric DNA is introduced into yeast by direct DNA transformation. Minichromosomes with inserts of DNA larger than 100 kb were identified. There are two problems with this system. First, yeast clones with inserts of DNA are generated very inefficiently; in the experiments described, about 300 clones were produced per microgram of insert DNA. Second, once clones with inserts of DNA are available, it is difficult to probe and recover the insert DNA. In transformed yeast cells, minichromosomes represent less than 1:200 of the total DNA of the cell and consequently can only be detected by DNA hybridization techniques. Moreover, within each transformed cell the inserts cannot be amplified. Segments of the insert can be recovered by subcloning into plasmids and rescuing into bacteria.

Another system of interest is described by Gaitanaies et al., Gene 46, 1-11 (1986). A lambda vector is described into which DNA can be inserted and which can then be injected into cells. The injected DNA is maintained in cells either integrated into the host's chromosome at one copy per cell or extrachromosomally in multiple copies per cell. While this vector can accommodate less than 30 kb of DNA, the amount of DNA in the integrated prophage can be increased significantly by homologous recombination with a second infecting lambda-chimera whose insert overlaps that in the integrated prophage. In this way the segment of contiguous DNA in any prophage can be increased to more than 100 kb and subsequently amplified by inducing the extrachromosomal state of the vector. However, to accomplish this, one needs to have cloned at least several contiguous and overlapping smaller segments of DNA and carry out an arduous process of stringing them together by recombination. Moreover, it will be difficult to recover the large DNA insert once it is constructed, since it will be too big to be packaged into a lambda virus-particle. Direct isolation of the DNA in its extrachromosomal state could also be difficult because of its large size.

Recently, Blumenthal, Focus, pages 41–46, Vol. 11, No. 3 (Summer 1989), reviewed some of the difficulties relating to cloning and restriction of methylated DNA in E. coli. The remedy suggested on page 45 is that such cloning (of methylated DNA) should be carried out in a host lacking the three known methylation dependent restriction systems including both components of the McrB system.

SUMMARY OF THE INVENTION

This invention relates to an in vitro headful packaging system for cloning foreign DNA fragments as large as 95 kb comprising:
(a) modifying vector DNA by inserting a stuffer fragment into a blunt end producing site which is proximal to a pac site;
(b) digesting the product of step (a) to produce two vector arms each of which contains (i) a blunt end, (ii) another end which is compatible with the foreign DNA fragment which is to be cloned, and (iii) a loxP site;
(c) ligating the foreign DNA to the product of step (b) without generating concatemers;
(d) reacting the product of step (c) with pac cleavage proficient extract and head-tail proficient extract wherein the ratio of large heads to small heads in the head-tail extract is at least 5:1;
(e) infecting a Cre+ bacterial strain with the product of step (d); and
(f) recovering the cloned DNA.

This invention also concerns a method of cloning and controlling amplification of DNA fragments as large as 95 kb in a vector containing a multicopy replicon under control of a lac promoter which comprises:
(a) ligating a DNA fragment to vector DNA;
(b) contacting the product of step (a) with a pac cleavage proficient extract and head-tail proficient extract;
(c) infecting a Cre+ bacterial strain having a lacI$^q$ repressor with the product of step (b);
(d) adding IPTG to culture medium; and
(e) recovering cloned and amplified DNA.

In another embodiment, this invention concerns vectors useful for cloning foreign fragments of DNA as large as 95 kb.

Lysogens to prepare pac-cleavage proficient extract and head-tail proficient extract constitute another aspect of the invention.

Cre+ gram-negative bacterial strains designated BS591, NS2974, and NS3145 were specifically engineered to be infected and transformed by the vectors of this invention. BS591 does not have a lacI$^q$ repressor gene. NS2974 and NS3145, on the other hand, do have a lacI$^q$ repressor gene and, thus, once transformed can repress the lac promoter until IPTG is added.

BRIEF DESCRIPTION OF THE DRAWINGS

FIG. 4 illustrates the construction of vectors pNS582tet14 and pNS582tet14Ad10.

FIGS. 8A–8C and 9A–9B illustrate recovery and characterization of the packaged pNS358 DNA and the E. coli inserts it contained.

FIG. 12 illustrates the ligation products generated when human DNA insert are ligated to either pNS582tet14 vector DNA or to the arms of pNS582tet14Ad10 vector DNA.

STATEMENT OF DEPOSIT

Figure 1:
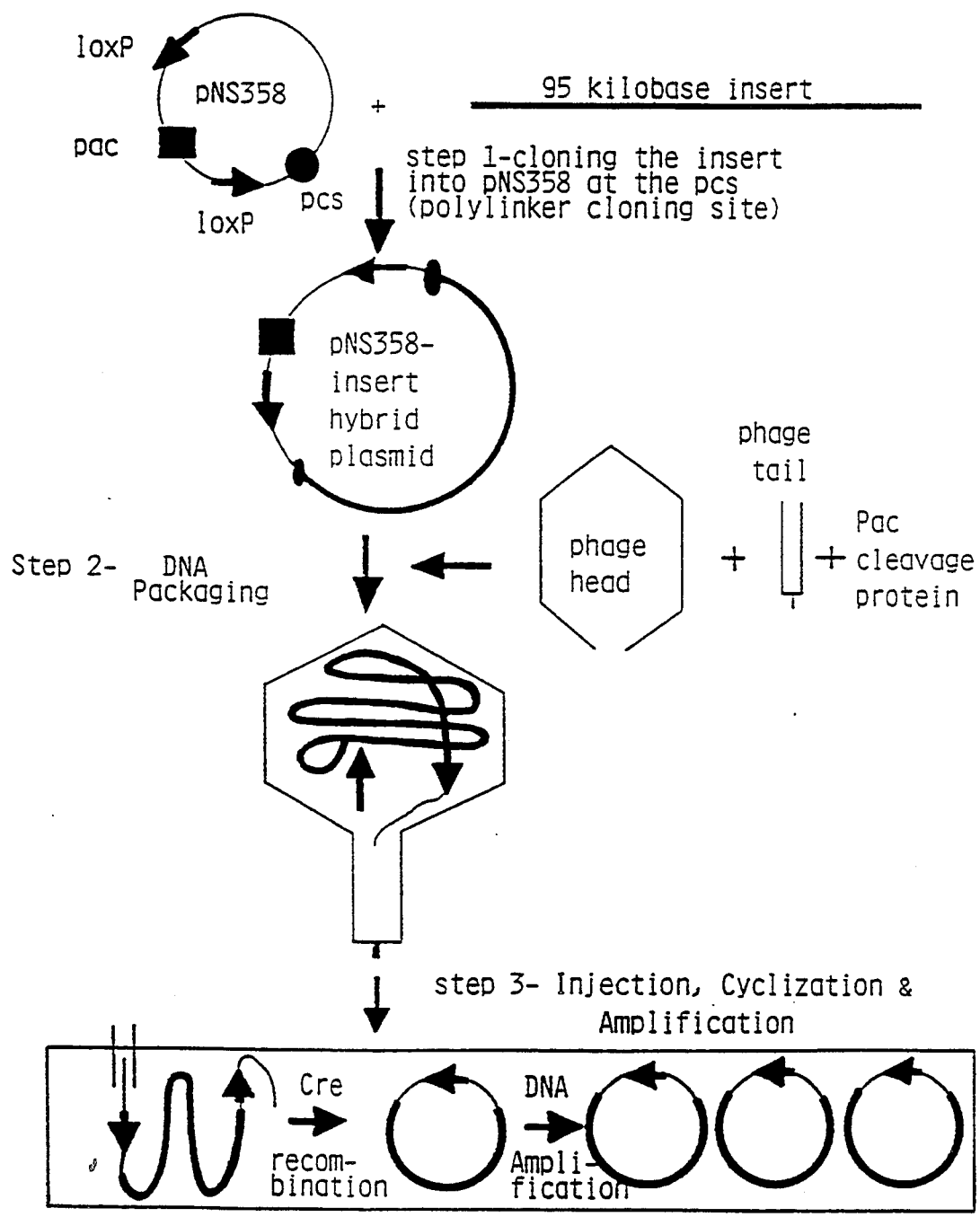
FIG. 1 illustrates generally the P1 bacteriophage cloning and amplification system.

The following bacteria and plasmids relating to the invention have been deposited in the American Type Culture Collection, 12301 Parklawn Drive, Rockville, Md. 20852-1776 under the Budapest Treaty.

pNS20 was designated ATCC Accession No. 67666.
pNS42 was designated ATCC Accession No. 67667.
BS591 was designated ATCC Accession No. 53760.
NS2961 was designated ATCC Accession No. 67665.
NS2962 was designated ATCC Accession No. 67664.
NS2974 was designated ATCC Accession No. 53759.
NS3208 was designated ATCC Accession No. 68073.
NS3210 was designated ATCC Accession No. 68074.
NS3145 was designated ATCC Accession No. 68072.

DETAILED DESCRIPTION OF THE INVENTION

The term pac is a generic name which refers to the site needed to initiate packaging of DNA.

The pac cleavage proficient extract contains the recognition proteins necessary to cleave the pac site and, thus, initiate packaging.

The head-tail proficient extract contains the heads and tails needed to package the cloned DNA into a virus particle.

The term concatemer means a DNA molecule consisting of repeating units arranged in a head-to-tail configuration.

The term stuffer fragment refers to a DNA fragment which is inserted into the vector DNA at a unique site, and within which headful packaging is terminated.

The terms bacteriophage and phage are used interchangeably herein.

The cloning system described herein utilizes a headful in vitro packaging system to clone foreign DNA fragments as large as 95 kb which permits the isolation of DNA fragments that are at least twice the size of those that can be obtained by lambda cosmid cloning. This increased cloning capacity has the following utility:

(1) Genes in the 45–95 kb size range and, more particularly, in the 70–95 kb size range can now be directly cloned and genes in the 25–45 kb size range can be cloned more easily.

(2) Chromosomal "walking" and "jumping" techniques can be speeded up by a factor of at least two and should be more accurate because of the reduced number of contiguous segments that need to be linked together.

(3) The cloning system of the invention is useful as a means for the delivery of DNA efficiently to bacteria which otherwise do not take up DNA from solution well.

Specifically, the headful packaging system of this invention for cloning foreign DNA fragments as large as 95 kb comprises:

(a) modifying vector DNA by inserting a stuffer fragment into a blunt end producing site which is proximal to a pac site;

(b) digesting the product of step (a) to produce two vector arms each of which contains (i) a blunt end, (ii) another end which is compatible with the foreign DNA fragment which is to be cloned, and (iii) a loxP site;

(c) ligating the foreign DNA to the product of step (b) without generating concatemers;

(d) reacting the product of step (c) with pac cleavage proficient extract and head-tail proficient extract wherein the ratio of large heads to small heads in the head-tail extract is at least 5:1;

(e) infecting a Cre+ bacterial strain with the product of step (d); and (f) recovering the cloned DNA.

Although many of the elements described herein pertain to the P1 bacteriophage cloning system, those skilled in the art will appreciate that, with the exception of the components needed to package DNA (pac and packaging extracts), many of the elements discussed below, such as the lox-Cre recombination system, plasmid replicon and a multicopy or lytic replicon, pertain to the recovery of packaged DNA and can be used to recover DNA in bacteria, such as *E. coli*, with other cloning systems, e.g., bacteriophage, yeast, etc.

Bacteriophages which are suitable to practice the invention must have a large head capacity and the elements necessary for packaging DNA must be defined. For example, for phages P22 and T1, which utilize headful packaging, the necessary packaging elements are defined. However, P22 and T1 do not have a very large head capacity. On the other hand, for phage T4, which has a large head capacity, the necessary packaging elements have not been defined.

Headful Packaging

The elements necessary for packaging DNA (i.e., an in vitro headful packaging system) are the following:

(1) a unique site, pac, which is cleaved by recognition proteins; it is the pac cleavage proficient extract which contains the recognition proteins necessary to cleave the pac site; and (2) empty phage heads into which the DNA is packaged until the head has been completely filled, then a cleavage event is triggered (the "headful" cut) which separates the packaged DNA away from the remaining components; it is the head-tail proficient extract which contains the heads and tails needed to package the cloned DNA into virus particle.

Although initiation of packaging is site-specific (cleavage of pac site initiates packaging), termination of packaging is not site-specific. In other words, no unique site is recognized, as packaging will terminate at whatever point the head has been filled.

In the case of P1, the DNA substrate used in the packaging reaction during the viral life cycle is a concatemer consisting of individual units of the P1 chromosome arranged in a head-to-tail manner. Headful packaging, using either P1 phage or any other phage, is a four step process: (1) In the first step a unique site, pac, is recognized and cleaved by the pac recognition proteins (PRPs); (2) DNA on one side of the cleavage is packaged into an empty phage head until the head has been completely filled; (3) a second cleavage event is then triggered (the "headful" cut) that separates the packaged DNA away from the rest of the concatemer; and (4) initiation of a second round of DNA packaging from the free end generated by the previous "headful" cut—hence the term processive headful cutting. However, if a concatemer is not generated then processive headful packaging does not occur. Sternberg et al., J. Mol. Biol. 194, 469–479 (1987), have described the cloning of a 161-bp sequence that contains a fully functional pac site. These studies also indicate that pac recognition and cleavage can occur in the absence of phage heads and tails, and is rendered non-functional by mutants in P1 gene 9 (see FIG. 2).

The ends of the packaged P1 DNA do not contain complementary single-stranded sequences, as do the ends of packaged bacteriophage lambda DNA, and consequently after P1 DNA is injected into a bacterium its cyclization does not occur by strand annealing but rather by recombination between homologous sequences present at the ends of the molecule. Because of this circumstance, any vector that uses P1 packaging, or for that matter any headful packaging mechanism, must devise a means of cyclizing the linear packaged DNA by recombination. In this invention, cyclizing was accomplished (see below) by incorporating loxP sites into the vector and using the Cre recombinase to cyclize the DNA after injection into Cre+, gram-negative bacterial strains.

P1 produces two head sizes, a big head that can accommodate 105–110 kb of DNA, and a small head that can accommodate no more than 45 kb of DNA. Normally the ratio of big to small heads in a P1 wild-type infection is 10:1, however, in the cm-2 mutant of P1 used to prepare some of the packaging lysates described herein, the radio of head sizes is 1:1. The head-tail packaging lysate prepared from the cm mutant of P1 contained the usual ratio of big to small heads which is about 10:1. This is the preferred lysate for preparing head-tail packaging extract. To ensure packaging of DNA exclusively into the big phage heads, the DNA must be bigger than that which can be accommodated by the small heads.

It is generally desired that there be a large excess of big heads. However, the ratio of large heads to small heads should not fall below a ratio of about 5:1.

The loxP-Cre Recombination System

This is a site-specific recombination system consisting of a 34-bp site or DNA sequence (loxP) at which recombination occurs very efficiently and a protein enzyme (Cre) that contacts the site and promotes the recombination. Abremski et al., Cell, 32, 1301–1311 (1983), showed that recombination between loxP sites on supercoiled, nicked circle, or linear DNA occured in the presence of Cre. In the P1 life cycle, Cre can promote recombination between loxP sites that are about 100 kb apart. The cre gene has been cloned into a lambda vector which expresses Cre when present as a lambda-P1:cre prophage in the *E. coli* chromosome. Sternberg et al., J. Mol. Biol. 187, 197–212, 1986, describe the pHR103 mutant containing the functional cre gene from which the prophage was constructed.

Figure 2:
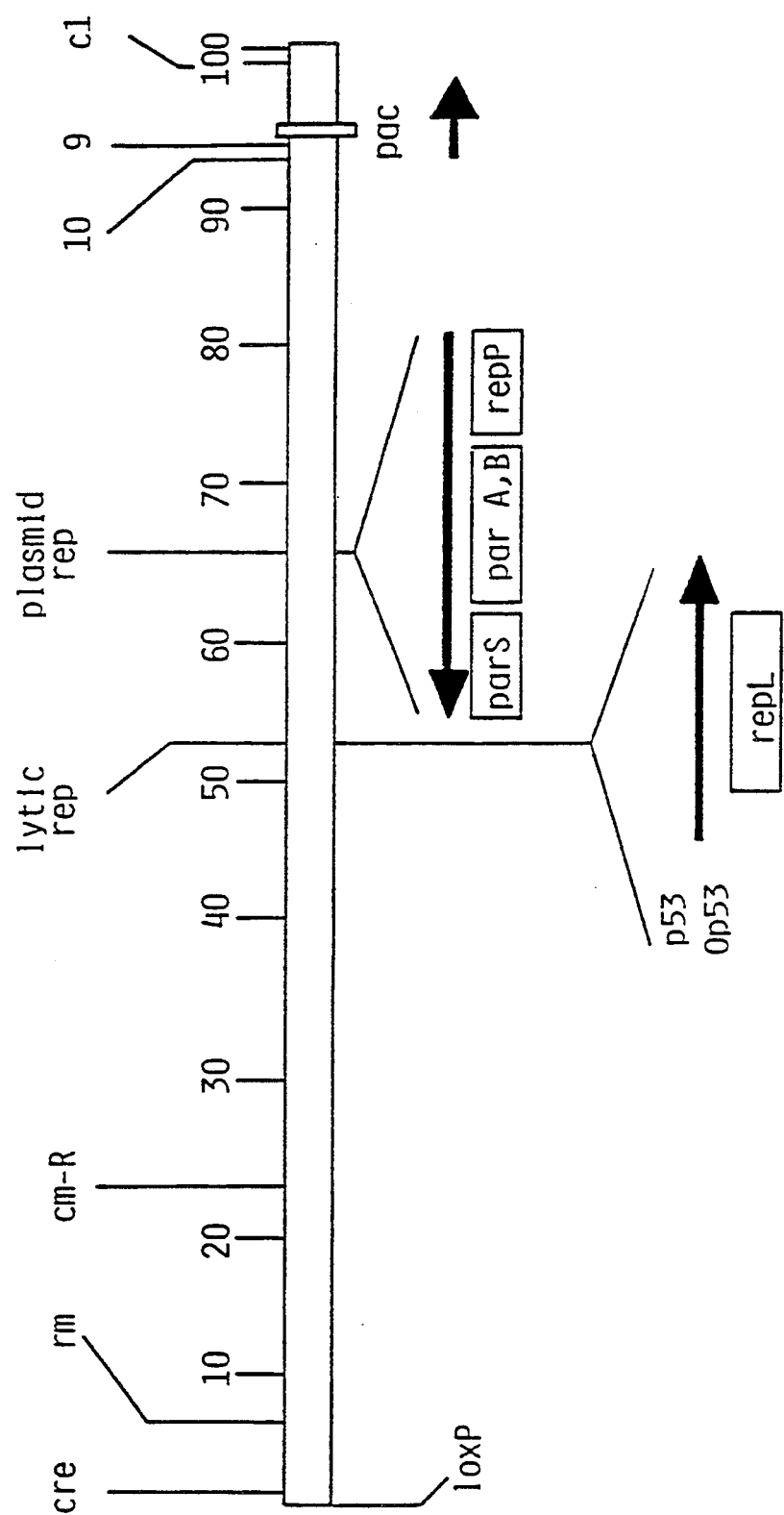
FIG. 2 maps the P1 genes and elements pertinent to the invention.

Many of the elements described herein, such as the lox-Cre recombination system, the P1 plasmid replicon, and the P1 lytic replicon, have also been recently reviewed in detail (Yarmolinsky & Sternberg, The Bacteriophage, Bacteriophage P1, Chapter 9, 1988, Plenum Publishing Corporation, 233 Spring St., New York, N.Y.). A map of P1 genes and the loxP-Cre recombination system, the P1 plasmid replicon, the P1 lytic replicon, and the pac site is shown in FIG. 2.

P1 Host Range

Bacteriophage P1 can adsorb to and inject its DNA into a variety of gram-negative bacteria that otherwise are unable to take up DNA efficiently. A tabulation of bacterial strains to which P1 virions can adsorb and inject DNA is shown in Table 1.

TABLE 1

Host Range of P1

| Bacterium | P1 DNA Injection | P1 Phage Production |
| --- | --- | --- |
| *Escherichia coli* K12,C,B | + | + |
| *Shigella dysenteriae* | + | + |
| *Shigella flexneri* | + | |
| *Salmonella typhimurium* | (−) + | + |
| *Salmonella typhi* & *abony* | + | |
| *Klebsiella aerogenes* | + | + |
| *Klebsiella pneumoniae* | + | + |
| *Citrobacter freundii* | + | + |
| *Serratia marcescens* | + | (−) + |
| *Enterobacter aerogenes* | + | + |
| *Enterobacter liquefaciens* & *cloacae* | + | + |
| *Erwinia carotovora* | + | + |
| *Erwinia amylovora* | + | + |
| *Yersinia pestis* & *pseudotuberculosis* | + | + |
| *Pseudomonas putida* | − | |
| *Pseudomonas aeruginosa* | + | (−) + |
| *Pseudomonas amyloderamosa* | | (−) ++ |
| *Flavobacterium* sp. M64 | + | − |
| *Argobacterium tumefaciens* | + | − |
| *Acetobacter suboxydans* | − | |
| *Alcaligenes faecalis* | + | − |
| *Myxococcus xanthus* | + | − |

Also tabulated is the ability of P1 to produce bacteriophages in these strains. With the ability to package DNA into P1 phage in vitro, it should be possible to clone DNA from any of these bacteria directly into a packaging vector, package that DNA into P1 virions, and then inject it back into those bacteria that are proficient for P1 injection. This all can be done without replicating the insert DNA in *E. coli* which would cause it to lose the methylation pattern that protects it from restriction enzymes when it enters its host of origin.

Bacterial Strains and Media

*E. coli* strains DH5 delta-lacU169, W3350, NS439, N99, JM101, JM109, 594 and YMC, or derivatives thereof, can serve as hosts for plasmids and phage P1. DH5 delta-lacU169 was obtained from Dr. Michael Berman, Litton Bionetics, and was a derivative of DH5, a variant of DH1 which was described by Hanahan, J. Mol. Biol. 166, 557–580 (1983). BS591 was DH5 delta-lacU169 (henceforth called DH5) with a lambda-imm434-P1 prophage that was constructed from a pRH103 mutant containing the Cre gene. The pRH103 mutant was described by Sternberg et al., in J. Mol. Biol. 187, 197–212 (1986). BS591 does not contain a lacI$^q$ repressor gene and it has the genotype recA− hsdM+ hsdR− mcrA+ mcrB+. JM101 and JM109 were obtained from New England Biolabs, Beverly, Mass. 01915, and were described by Yanish-Perron et al., in Gene 33, 102–119 (1985). NS2974 was JM109 and has a lambda-imm434-P1 prophage containing a functional Cre gene and a lacI$^q$ repressor. The genotype of NS2974 is recA− hsdM+ hsdR− $^{mcrAB+}$ (mcrA+, mcrB+). Strains 594 and W3350 were described by Campbell et al., Carnegie Institute of Wash. Yearbook 57, 386 (1987); YMC was described by Dennert et al., J. Mol. Biol. 33, 322–329 (1968), N99 was described by Shimada et al., J. Mol. Biol. 93, 483–503 (1972). The genotype of N99 is recD+ hsdR+ hsdM+ mcrA+ mcrB+. NS439 was strain YMC with a trpE 5947 mutation. NS3067 was NS439 and has a lambda-imm434-P1prophage with a functional cre gene. Media (i.e., L broth and L-amp agar) for bacterial growth were described in Miller, Experiments in Molecular Genetics (Cold Spring Harbor Laboratory, Cold Spring Harbor, N.Y., 1972).

NS3145 was constructed starting with strain NM554 (obtained from New England Biolabs). NM554 has the genotype recA− hsdM+ hsdR− mcrA− mcrB−. An F'lacI$^q$ plasmid was first transferred into this strain by conjugal mating as described in Miller, Experiments in Molecular Genetics (Cold Spring Harbor Laboratory, Cold Spring Harbor, N.Y., 1972), and the resulting strain (NS3100) was then infected with the lambda immunity 434-P1 Cre-containing prophage. Lysogens were selected as described in Sternberg, Virology, pages 129–142, Vol. 96 (1979), and one of those lysogen was designated NS3145.

Phage Methods

P1 phage (P1 bacteriophage, P1) manipulations, including the preparation of phage lysates, making phage genetic crosses, doing phage complementation tests, and bringing about phage lysogenization were described by Sternberg et al., in J. Mol. Biol. 187, 197–212 (1986) and by Sternberg et al., in J. Mol. Biol. 194, 453–468 (1987).

DNA Preparation and Manipulation

Plasmid DNA smaller than 20 kb was prepared from *E. coli* according to (1) the rapid method (hereafter referred to as rapid plasmid preparation) described by Holmes & Quigley in Anal. Biochem. 114, 143–197 (1981) or (2) the cesium chloride density gradient method as described by Godson and Vapnek, BMA 299, 516–522 (1973). Plasmid DNA bigger than 20 kb was prepared by the method of Birnboim et al., Nucl. Acids Res. 7, 1513–1523 (1979). Cellular DNA was isolated from *E. coli* as described by Sternberg et al., J. Mol. Biol. 194, 469–479 (1987). To maintain the size of the DNA above 200 kb, care was taken to avoid shear forces during this isolation procedure. Pulse field agarose gel electrophoresis was carried out as described by Carle et al., Science 232, 65–68 (1986). Restriction enzyme digestion of DNA and DNA ligation with T4 DNA ligase should be done as specified by the vendor, which was in our case, New England Biolabs. All other methods of manipulating DNA were described by Maniatis et al., Molecular Cloning: A Laboratory Manual (Cold Spring Harbor Laboratory, Box 100, Cold Spring Harbor, N.Y. 1982).

Preparation, Digestion and Size Fractiontion of High Molecular Weight Human DNA

Human lymphoblastoid cell line 697 (Kaplan et al., Biochem. Biophys. Res. Comm., pages 1275–1282, Vol. 159 (1989)) was used as a source of DNA. That DNA was prepared as follows: cells growing in suspension culture were collected by centrifugation (4,000 rpm in an RT6000 rotor) washed once with phosphate-buffered saline (PBS) and a second time with 50 mM Tris-HCl pH 7.5, 100 mM NaCl. The cells were then resuspended in 2 ml of the latter buffer and the following components were added: proteinase K to 1 mg/ml, EDTA to 120 mM, SDS to 0.5% and water to bring the volume to 4 ml. The suspension was then incubated for 2 hours at 50° C. and then extracted first with 4 ml of phenol and then with 4 ml of chloroform-isoamyl alcohol (24:1) saving the aqueous layer each time. The aqueous layer was then dialyzed against 4 changes of 1 liter each of 10 mM Tris-HCl pH 8.0–1 mM EDTA at 4° C. Each change was dialyzed for 8 hours.

10 $\mu$g of dialyzed high molecular weight DNA was incubated at 4° C for 12 hours with gentle agitation in 100 $\mu$l 1X restriction buffer (20 mM Tris-HCl, pH 8.0, 100 mM NaCl), without $Mg^{++}$, with bovine serum albumin (100 $\mu$g/ml) and with 1–10 units of restriction enzyme (BamHI or Sau3AI). This $Mg^{++}$ depleted incubation was designed to ensure uniform mixing of the viscous DNA with enzyme prior to starting the reaction. 10 $\mu$l of a 100 mM $MgCl_2$ solution was then added to each reaction tube, the contents of the tubes were gently mixed with the tip of a pipette and the tubes were immediately incubated at 37° C. The reactions were stopped after 5 minutes by adding 10 $\mu$l of a solution of 200 mM EDTA to the tubes and then placing them at 4° C. Samples of approximately 5 $\mu$l were removed from each tube and subjected to field inversion gel electrophoresis (described below) to assess the extent of the restriction reaction. Reactions in which at least 50% of the DNA had been digested to a size ranging from 30–200 kb were further fractioned on sucrose gradients. Field inversion electrophoresis was carried out for two hours in 1% agarose gels made up in Tris-borate-EDTA buffer (0.089M Tris-Borate, 0.089 boric acid, 0.002M EDTA) at 230 volts with a forward pulse of 0.6 sec, a backward pulse of 0.2 sec, and a ramp factor of 20.

Thirty five ml 10–50% sucrose gradients were prepared as described in Maniatis et al., Molecular Cloning: A Laboratory Manual (Cold Spring Harbor Laboratory, Box 100, Cold Spring Harbor, N.Y., 1982). The appropriate EDTA-stopped reactions prepared above were layered on top of these gradients and the gradients were centrifuged for 15 hours at 20,000 rpm in a SW27 swinging bucket Sorvall rotor at 4° C. The gradient was then collected in 1 ml fractions into 24-well tissue culture dishes as follows. The top of the centrifuge tube was wrapped with parafilm and carefully clamped to a stand. The bottom of the tube was punctured with an 18 gauge needle and the needle then gently removed. To start the gradient dripping, the parafilm cover was punctured with a needle. The flow rate was regulated by finger pressure provided to the top hole. After analyzing the size of the DNA in each gradient fraction by field inversion gel electrophoresis the appropriate fractions were pooled and then concentrated by n-butanol extraction. First, the pooled fractions were dialyzed by pipeting them onto a VSWP 02500 filter (Millipore) that was floated on the surface of a 10 mM Tris-HCl pH 8.0-1 mM EDTA buffer. Usually 1–2 ml of sample could be completely dialyzed against the 500 ml of buffer in about 2 hours at 25° C. The dialyzed samples were then mixed with 2 volumes of n-butanol in a 2059 falcon tube and the mixture gently rocked until volume of the aqueous phase was reduced 2–3 fold. The tube was centrifuged for 2 minutes at 2000 rpm and the top butanol phase removed. These steps were repeated until the aqueous phase was reduced to about 40–50 $\mu$l. The residual butanol was then allowed to evaporate for 10 minutes at room temperature and then the samples were dialyzed on filters against 10 mM Tris-HCl pH 8.0–1 mM EDTA for 30 minutes to remove any residual salt.

Figure 10:
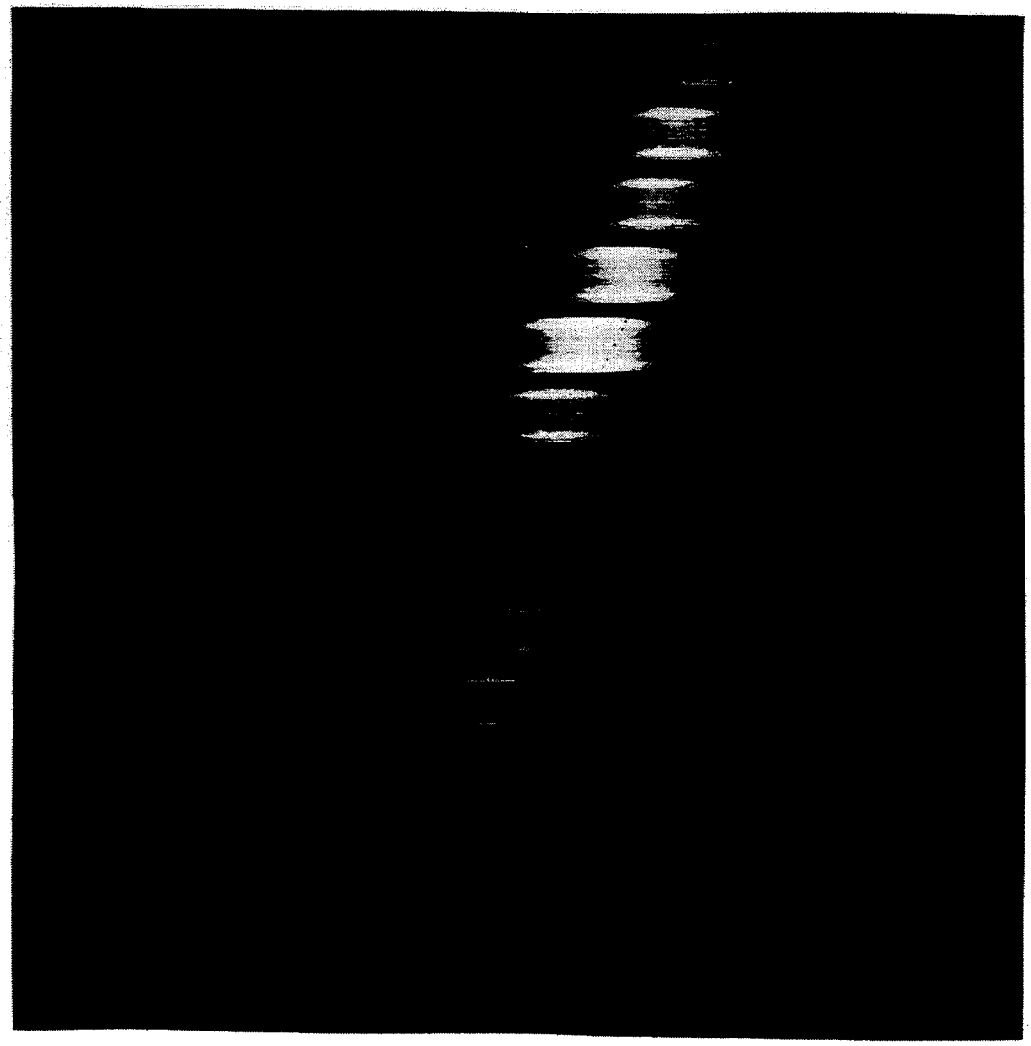
FIG. 10 illustrates the recovery of size fractionated human insert DNA by sucrose gradients.

An analysis of sucrose gradient-fractionated SaU3AI-digested human DNA by field inversion gel electrophoresis is shown in FIG. 10. Comparing the size of the fragments in the various lanes to the size of 165 kb and 50 kb DNA markers in lane M it is clear that fragments in lanes 6–10 spanned the desired 50–110 kb range for cloning into the P1 vectors. Lane T contained the original unfractionated Sau3AI-digested DNA.

Southern Analysis

DNA was transferred to nitrocellulose membranes from agarose gels and probed with specific labeled DNA fragments or plasmids according to the method of Southern, J. Mol. Biol. 98, 503–507 (1975), henceforth referred to as "Southern analysis". DNA was sequenced using the dideoxy nucleotide procedure of Sanger et al., Proc. Natl. Acad. Sci., USA, 74, 5463–5467 (1977).

Restriction Analysis

Five hundred nanograms of DNA was digested with 1–2 units of restriction enzyme for 2 hours at 37° C. in 20 microliters of a buffer specified by New England Biolabs (Beverly, Mass. 01915), from whom the enzyme was purchased. The reaction was stopped by adding 3 microliters of a solution of 0.25% bromophenol blue, 0.25% xylene cyanol, and 40% (w/v) sucrose, followed by heating the reaction to 70° C. for 5 minutes. The samples were loaded into the slots of a 1% agarose gel (15×15 cm) that was submerged in a Tris-Borate-EDTA buffer (0.089M Tris-Borate, 0.089 boric acid, 0.002M EDTA). Electrophoresis was carried out at 20 milliamps (30 volts) until the xylene cyanol band migrated two-thirds of the way into the gel, usually about 12 hours at room temperature. The gel was then stained in a solution 0.5 micrograms/ml of ethidium bromide for 30 minutes, and a picture of the gel was taken using a transmitted UV light source (320 nm) and polaroid type 57 film.

Treatment of DNA with alkaline phosphatase (AP)

After DNA was digested by restriction enzymes as described in the previous section, it was heated to 70° C. for 5 minutes The reaction was cooled to 37° C., brought to 100 microliters with a 10 mM Tris-HCl pH 8.0 solution, and then incubated with 0.01 units of calf intestine alkaline phosphatase for 1 hour at 37° C. The reaction was extracted 4 times with an equal volume of phenol and once with an equal volume of chloroformisoamyl alcohol (24:1) and the DNA then precipitated in 1M LiCl₂ with 2 volumes of ethanol at −20° C. for 3 hours.

Ligation and Insertion of DNA Fragments into Vectors

Ligation reactions were carried out in a volume of 20 microliters containing 6 mM Tris-HCl pH 7.5, 5 mM MgCl₂, 5 mM dithiothreitol, 1 mM ATP, 100 micrograms/ml bovine serum albumin. For reactions involving the insertion of fragments into plasmids that were to be recovered by transformation into competent bacteria, 100 ng of digested vector DNA and 100–400 ng of insert fragment were used. For reactions involving plasmid vectors that were to be recovered by in vitro headful packaging, 500 ng of vector DNA and 1-2 micrograms of insert fragment were used. 400 units of T4 ligase were added for each reaction and the reactions were incubated for 20 hours at 16° C. The reactions were stopped by heating to 70° C. for 10 minutes.

As is described in Example 4 below, one of the unique aspects of this invention is the ability to ligate foreign DNA to vector DNA without generating concatemers.

Concatemer generation was avoided by digesting the vector DNA at two different restriction sites to produce two vector fragments (arms). Each arm contains one end which cannot ligate to DNA insert, cannot ligate to itself, and is not recovered during cyclization of the packaged DNA. Each arm contains another end which is free to ligate with the DNA which is to be cloned. After fragment ligation to the arms, the resulting product contains the DNA to be cloned sandwiched between the vector arms produced by the double digestion. The ends of this ligation product cannot be ligated further and, thus, concatemer formation is prevented.

The end which cannot ligate further is preferably generated by cleaving a blunt end producing site which is unique to the vector DNA. For example, in the experimental section below, the blunt end producing site was a ScaI site. This blunt end producing site can be naturally occurring or artificially created.

The end which is free to ligate should be compatible with the insert ends of the DNA to which it will be ligated. In addition, this sequence is recovered during cyclization, whereas the unique blunt end producing site is not recovered during cyclization.

Selection of Transformants

E. coli strains were transformed according to (1) a method of Mandel and Higa, J. Mol. Biol. 53, 159–162 (1970) or (2) a method of Hanahan, J. Mol. Biol. 166, 557–580 (1983) when high efficiency was required. Transformed cells in a volume of 0.1 ml were diluted to 1 ml with L-broth and incubated for 1 hour at 37° C. 100–200 microliters of the culture was spread onto L agar plates containing either kanamycin (25 microliters/ml) or ampicillin (150 micrograms/ml) and the plates incubated for 16 hours at 37° C. Colonies were then scored. Amp-R transformants were tested for growth on L-agar plates with kanamycin and vice versa.

Construction of the Plasmid Vector, pNS358-lyt (pNS582)

The plasmid vector identified as pNS358-lyt is also identified as pNS582. Thus, the terms pNS358-lyt and pNS582 are used interchangeably herein.

Figure 3:
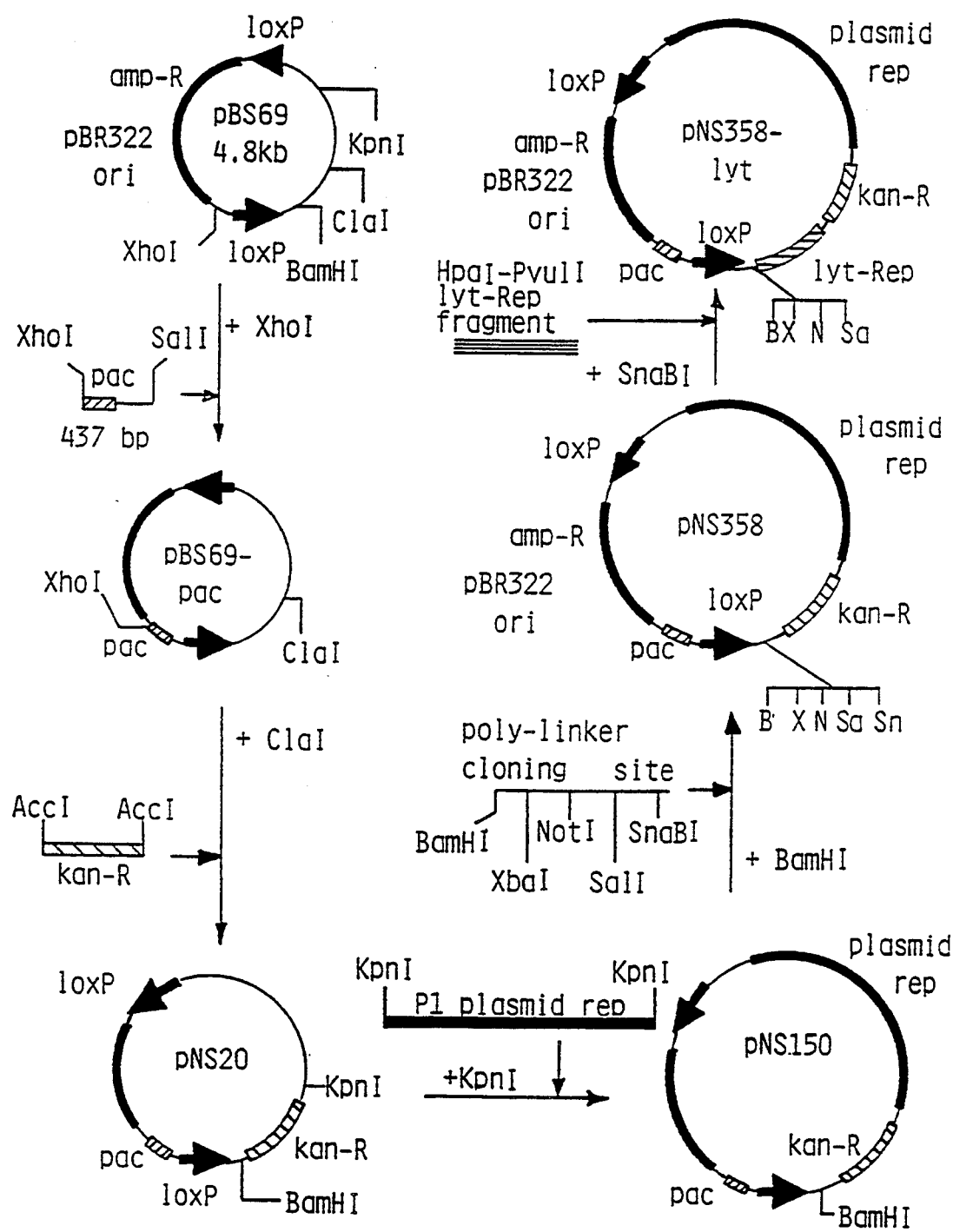
FIG. 3 illustrates the construction of the vectors of the instant invention.

A flow sheet describing the various steps in the construction of the vector is shown in FIG. 3. The starting plasmid was pBS69. It was a 4.9 kb plasmid containing two loxP recombination sites orientated in the same direction. In the presence of Cre protein, recombination occurs between these sites to generate two circles of DNA, each containing one loxP site and one of the two regions of DNA between the loxP sites in pBS69. One of these circularized regions, henceforth called the amp-R domain, contained the gene that codes for resistance to the drug ampicillin and the DNA replicating system (replicon or origin of replication [ori]) of the plasmid pBR322 (hereinafter pBR322 ori). The other circularized region between the loxP sites of pBS69 contained the yeast leu2 gene.

(a) Insertion of the P1 packaging site, pac, into pBS69

The P1 sequences necessary for the intiation of DNA packaging were localized to a 161 bp segment of DNA (pac site). This segment of DNA represented the P1 sequences remaining in the double-deletion mutant (delta-3-delta-20) described by Sternberg et al., J. Mol. Biol. 194, 469–479 (1981). Delta-3–delta-20 DNA was digested with restriction enzymes XhoI and SalI and a 437 bp fragment containing the 161 bp pac site was isolated and ligated to the unique XhoI site in the amp-R domain of pBS69 DNA. The resulting pBS69-pac plasmid contained pac oriented such that packaging would occur counterclockwise as the plasmid is drawn in FIG. 3. In addition to pac, the 437 bp insert contained the tetracycline resistant gene sequences located between pBR322 map coordinates 375 and 651. Also, the BamHI site, present in the 437 bp DNA fragment and located between pac and the pBR322 sequences in the plasmid DNA, was deleted. Removal of the BamHI site ensured that the pBS69-pac plasmid would have only the single pBS69 BamHI site.

(b) Insertion of the Tn903 Kanamycin-resistance gene into pBS69-pac to generate pNS20

The Tn903 kanamycin resistance (kan-R) gene was isolated as a 1.3 kb AccI fragment from plasmid puc4K, which was purchased from PL-Biochemicals (Milwaukee, Wis.). pBS69-pac DNA was digested with the restriction enzyme ClaI, which cleaved that DNA once within the yeast leu2 gene. Equal amounts (100 ng) of that digested plasmid DNA and the kan-R gene fragment were mixed in 20 microliters and ligated overnight at 16° C. The ligation mix was used to transform strain DH5 bacteria and kan-R, amp-R transformants selected. Analyses of rapid plasmid preparations made from these transformants indicated that they all contained the kan-R gene at the ClaI site of pBS69-pac. The plasmid chosen for all subsequent manipulations, henceforth designated pNS20, contained the kan-R fragment oriented such that the direction of kan transcription was counterclockwise (FIG. 3). The region flanked by loxP sites containing this kan-R gene will henceforth be designated the kan-R domain.

(c) Insertion of the P1 plasmid replicon into pNS20 to generate pNS150

The P1 plasmid replicon and partition region is responsible for maintaining the P1 prophage as a unit copy extrachromosomal element in a population of lysogenic cells. It contains a replication gene (repP) that encodes a protein which acts at an origin sequence in the DNA to initiate a single round of replication per cell division cycle. Also present in the replicon are two genes, parA and parB, that act at a site, parS, to faithfully partition the products of replication to daughter cells at cell division.

A 7 kb KpnI fragment of DNA, located between P1 map coordinates 59 and 66 (FIG. 2), was isolated after digesting the DNA from P1 phage with KpnI. It was ligated into the unique KpnI site of pNS20, and its presence in the plasmid was confirmed by analyzing restriction enzyme digests of rapid plasmid preparations. The particular construct chosen for further manipulation was designated pNS150 and contained the P1 DNA from map coordinate 59 to 66 oriented counterclockwise in the plasmid. The 7 kb P1 insert contained not only the plasmid replication system, but also its partition system (Yarmolinsky and Sternberg, in "The Bacteriophages", Chapter 9, 1988).

(d) Insertion of a polylinker cloning site into pNS150 DNA to generate pNS358

Two 31 base oligodeoxynucleotides with complementary sequences were synthesized by the phosphoramidite method. 10 micrograms of each oligonucleotide in a volume of 100 microliters (10 mM Tris-HCl buffer at pH 8.0, 1 mM EDTA) were annealed to each other at 70° C. for 10 minutes. The resulting double stranded fragment is shown below:

GATCCTCTAGAGCGGCCGCGTCGACTACGTA
  GAGATCTCGCCGGCGCAGCTGATGCATCTAG
  <u>XbaI</u>   <u>NotI</u>   <u>SalI</u>   <u>SnaBI</u>

This fragment of DNA contained, from left to right, the following restriction endonuclease sites: XbaI (X)-AGATCT; NotI (N)-CGCCGGCG; SalI (Sa)-CAGCTG; SnaBI (Sn)-ATGCAT. None of these sites were present in the DNA of pNS150. The fragment also contained single-stranded GATC ends that were complementary to the ends generated by BamHI digestion. Because the nucleotides 3' to the GATC ends of the fragment were different, ligation of this fragment to DNA with BamHI ends regenerated a BamHI site on one side of the insert but not on the other. The fragment was ligated to BamHI-cleaved pNS150 DNA and the presence of the insert was confirmed by the ability of the plasmid to be cleaved only once by each of five restriction enzymes BamHI, XbaI, NotI, SalI, and SnaB1. The particular construct chosen for further manipulation was designated pNS358 and had the polylinker from BamHI to SnaBI oriented counterclockwise on the plasmid (FIG. 3).

(e) Insertion of the P1 lytic replicon into pNS358 to generate pNS358-lyt (PNS582)

The P1 vegetative or lytic replicon can replicate DNA to a high copy number within 30 minutes after prophage derepression. This replicon consists of a transcription promoter P53 and a downstream repL gene whose product acts at an origin sequence to promote replication. The replicon is negative regulated by the phage c1 repressor that binds to P53 and prevents transcription of the repL gene.

The P1 lytic replicon was cloned as a 1.9 kb AsuII fragment (P1 map coordinates 53–55) in which the normal P53 promoter was replaced by the lac promoter. Thus, the P1 lytic replicon was placed under the control of the lac promoter. The lac promoter is in turn controlled by the lacI$^q$ repressor. In the presence of IPTG (isopropyl-beta-D-galactoside) the lacI$^q$ repressor is derepressed and the replicon becomes functional. The lac promoter-regulated P1 lytic replicon was isolated as a PvuII-HpaI fragment from plasmid pNS42 and ligated to SnaBI-digested pNS358 DNA, to generate the pNS358-lyt plasmid. The replicon (P1 map coordinates 53–55) was oriented counterclockwise in the plasmid.

Thus, in another aspect this invention concerns controlling amplification of cloned DNA using a lac promoter which is under the control of a lacI$^q$ repressor until IPTG is added to derepress the repressor.

Construction of Plasmid Vectors pNS582tet14 and pNS582tet14Ad10

A flow sheet describing the various steps in the construction of the above two vectors is shown in FIG. 4. To produce pNS582tet14, DNA from plasmid pNS582 (FIG. 3) was digested with restriction enzymes BamHI and SalI, both of which cleave the DNA in pNS582's polylinker cloning site. At the same time, DNA from plasmid pBR322 was digested with restriction enzymes EcoRI and NdeI which cleaves pBR322's tetracycline-resistance (tet-R) gene away from the rest of the plasmid. The tet-R gene is present on a 2.3 kb DNA fragment. Both of the DNA digests were next incubated with dATP, dTTP, dGTP, and dCTP and with DNA polymerase I Klenow fragment (Boehringer-Mannheim) as described in Maniatis et al., Molecular Cloning: A Laboratory Manual (Cold Spring Harbor Laboratory, Box 100, Cold Spring Harbor, N.Y., 1982), to fill-in the single-stranded ends generated by the restriction enzyme cleavage reactions described above. The restriction enzymes and Klenow fragment were inactivated by heating the final reaction to 70° C. for 15 minutes. Equal amounts (500 ng) of the two digested and filled-in plasmid DNAs were mixed in 20 µl of ligation buffer as described above and ligated overnight at 16° C. in the presence of T4 DNA ligase. The ligation mix was used to transform strain DH5 bacteria and kanR, amp-R, tet-R transformants selected. Analyses of rapid plasmid preparations made from these transformants indicated they contained the tet-R gene fragment inserted between the BamHI and SalI sites of the polylinker cloning site of the pNS582 DNA. In the cloning process the latter two sites were destroyed and DNA sequences between them (including the unique NotI and XbaI sites) were deleted. The tet-R gene contained one BamHI site and one SalI site within its coding region. In pNS582tet14 DNA these sites are unique and cloning DNA into those sites interrupts the tet-R gene. Those clones are easily recognized because they are tetracycline-sensitive.

To produce pNS582tet14Ad10, pNS582tet14 DNA was digested with the restriction enzyme ScaI, which cleaves it once in the amp-R gene. At the same time Adenovirus DNA (Sigma) was digested with restriction enzymes ScaI and BamHI to produce an approximately 10 kb ScaI-BamHI fragment. The latter digest was incubated with the four deoxynucleotide triphosphates and Klenow fragment (described above) to fill in the single-stranded ends generated by BamHI (ScaI digestion naturally produces blunt ends). Equal amounts (500 ng) of the two digested DNAs were mixed in 20 µl of ligation buffer as described above and ligated overnight at 16° C. The ligation mix was used to transform strain DH5 bacteria and kan-R, tet-R, amp-S transformants selected. Analysis of rapid plasmid preparations made from 10 of these transformants indicated that one transformant contained an approximately 10.6 kb ScaI-BamHI fragment from Adenovirus DNA cloned into the ScaI site of pNS582tet14 DNA. The orientation of this fragment in the vector is such that its ScaI end was proximal to the pac site (FIG. 4). Since ligation of a filled-in BamHI end to a ScaI end generates a DNA sequence that cannot be cleaved by either of those two enzymes, pNS528tet14Ad10 DNA contained only a single ScaI site.

The purpose of the Adenovirus fragment was to provide a large (>5 kb) DNA fragment in which headful packaging could terminate. In its absence, termination of headful packaging would be relegated to a short 400 base pair region between the ampR gene proximal loxP site and the ScaI site within the ampR gene, a circumstance that would severely limit cloning of inserts in the absence of concatemerization. The Adenovirus fragment is termed a "stuffer" fragment, as it is stuffed into the vector DNA simply to provide more DNA for the termination of packaging. The site into which the stuffer fragment is cloned is not recovered during cyclization of packaged DNA.

In addition, any DNA can be used as the stuffer fragment, it need not be Adenovirus DNA. Some considerations which enter into the selection of stuffer fragment DNA include: (1) the ease with which the stuffer fragment can be inserted into the vector DNA blunt end producing site such that this site is remains unique in the vector DNA and is proximal to the pac site; and (2) the source of the DNA which will serve as the stuffer fragment should be readily available. For example, Adenovirus DNA is commercially available.

The size of the stuffer fragment can vary from about 5 kb to about 20 kb, depending upon the size of the DNA which is to be recovered in the cloning process. The size of the stuffer fragment determines the size range, within 5–10 kb, of DNA which will be recovered.

For example, if the initial population of DNA molecules is of variable size and the size of the DNA to be recovered is about 90–95 kb, then the preferred size of the stuffer fragment should be relatively small. Concomitantly, the cloning efficiency will be low because there will be only a few DNA molecules in the narrow size range (90–95 kb) that can be cloned. Indeed, the stuffer fragment could be eliminated altogether if the insert DNA is large enough to allow packaging to terminate within the 400 base pair region mentioned above.

If the size of the DNA to be recovered is about 70–85 kb in size, then the stuffer fragment should be about 10 kb in size. If the size of the DNA to be recovered is about 60–75 kb the preferred size of the stuffer fragment should be about 20 kb.

Construction and Properties of Phage and Lysogens Used in Generating P1 Packaging Extracts The phage used to construct lysogenic bacteria (lysogens) for the preparation of P1 packaging extracts were the quadruple mutants P1rm$^-$cm$-$2c1.100 9.16 or P1rm$^-$cm$-$2c1.100 10.1. The properties of the individual mutations, and the reason for their incorporation in the final phage, are discussed below.

(a) c1.100. This mutation, first described by Rosner, Virology, 48, 679–689 (1972), renders the phage c1 repressor temperature sensitive. Thus lysogens containing this P1 prophage grow normally at temperatures below 33° C. but are induced to enter the lyric cycle and produce phage at higher temperatures. For example, if the temperature of the culture is raised from 33° C. to 40° C., and the culture is held at that temperature, cell lysis starts to occur within 50 minutes of the shift and about 100 phage/cell are released.

(b) rm$^-$. This mutation, first described by Glover et al., Genet. Res., 4, 480–482 (1963) renders the restriction and modification system of the virus inactive. It was incorporated into the phage used here so that extracts made from induced P1 lysogens would not contain a restriction endonuclease activity that could destroy added DNA before it might be packaged.

(c) cm-2. This mutation is described in Iida and Arber, Mol. Gen. Genet., 153, 259–269 (1977) and is a gross chromosomal rearrangement in which a Tn9 transposon, with its chloramphenicol resistance (cm-R) gene, was inserted at P1 map coordinate 24 and a 10 kb portion of P1 DNA between map coordinates 24 and 33 was deleted. The mutation renders the phage partially lysis defective so that following induction of a lysogen, bacteria can be harvested at later times than is otherwise possible. Another property of this mutant is that it produces more small-headed phage variants than does wild-type P1.

cm is a mutant containing the Tn9 transposon at P1 map coordinates 24 without the associated 10 kb deletion of P1 DNA.

(d) am9.16 and am10.1. P1 amber (am) mutant 10.1 contains a nonsense mutation in P1 gene 10 (see FIG. 2) and is defective for all "late" phage protein synthesis. It produces a normal amount of pac-cleavage activity. P1 amber mutant 9.16 contains a nonsense mutation in P1 gene 9 and is defective for the production of pac-cleavage activity. It produces phage morphogenesis proteins normally, including phage heads and tails. While extracts prepared from either one of these mutants are not expected to be able to package DNA in vitro, both extracts together should have all the needed components for packaging.

P1 amber mutant 131 also contains a nonsense mutation in P1 gene 9 and is defective for the production of pac cleavage activity.

(e) The quadruple phage mutants were constructed in a two-step process. First, phages P1 cm-2 and either P1 c1.100 9.16 or P1 c1.100 10.1 were crossed and recombinant phage containing the three mutations, P1 cm-2 c1.100 9.16 or P1 cm-2 c1.100 10.1, were selected. The phage produced by this cross were used to generate plaques on a bacterial lawn of strain YMC and individual plaques screened for the following three properties: (1) the ability to produce lysogens that were cm-R; (2) temperature sensitivity; and (3) the ability to make plaques on bacterial strain YMC but not on strain N99. The former strain contained an amber suppressor while the latter did not. To confirm that amber mutant recombinants contained the correct amber mutation, complementation experiments with control 9.16 and 10.1 phages were carried out. Amber mutants in the same gene will not complement each other for phage production but those in different genes, like genes 9 and 10, will. The complementation tests confirmed that the amber mutations in the triple mutants were those expected based on the phage used to generate those mutants. The triple mutants were next crossed with P1rm− and the quadruple mutants were identified as having all of the properties of the triple mutants plus the inability to restrict the growth of phage lambda when present as a prophage in any E. Coli strain. P1c1.100rm−cmam131 was constructed as were the other guadruple mutants except that the two starting phages were P1cm and P1c1.100am131.

The quadruple P1 mutants were used to lysogenize strain N99 and those lysogens, designated NS2961 and NS2962, respectively, for the 9.16 and 10.1 mutants, were used to prepare P1 extracts for the in vitro packaging reaction. Furthermore, these P1 mutants can also be used to lysogenize any bacterial strain proficient for their uptake. NS2961 and NS2962 have the genotype recD+ hsdR+ hsdM+ mcrA+ mcrB+.

To construct P1 lysogens NS3205, NS3208, and NS3210, bacterial strain MC1061 (obtained from New England Biolabs) whose geneotype is recA+ hsdM+ hsdR− mcrA− mcrB− was used. This strain was made recD− by P1 transduction of a recD− mutation linked to an adjacent tetracycline resistant gene as described in Miller, Experiments in Molecular Genetics (Cold Spring Harbor Laboratory, Cold Spring Harbor, N.Y., 1972). The resulting strain was then lysogenized with either P1c1.100cm−2rm− am9.16 or P1c1.100cm−2rm−am10.1 or P1c1.100cmrm−am131 to generate either NS3205, NS3208 or NS3210, respectively. NS3205, NS3208 and NS3210 have the genotype recD− hsdR− hsdM+ mcrA− mcrB−. Note that the P1 prophages in NS3205 and NS3208 have the cm-2 mutation which not only contains the Tn9 transposon with its cm-R gene but also contains an adjacent deletion of P1 DNA. In contrast, NS3210 contained only the Tn9 transposon, designated here cm. Head-tail packaging extracts prepared from the lysogen designated NS3210 contained the normal ratio of phage large heads to small heads of about 10:1. In practicing the invention, the ratio of large heads to small heads should be at least about 5:1.

Preparation Of P1 Packaging Extracts (a) Preparation of the 10.1 or pac-cleavage proficient (pcp±) extract One liter of L broth was inoculated with a colony of strain NS2962 bacteria and the culture grown at 32° C. to an OD650 of 0.8. The temperature of the culture was then rapidly raised to 42° C. by swirling it in a 90° C. water bath and growth continued with vigorous aeration at 42° C. for 15 minutes. The temperature of the culture was then lowered by placing it in a 38° C. water bath and vigorous aeration continued for an additional 165 minutes. The bacterial suspension was then rapidly chilled to 4° C. in an ice slurry and pelleted by centrifugation at 6000× g for 10 minutes at 4° C. in a Sorvall GSA rotor. The cell pellet was resuspended in 2 ml of a buffer consisting of 20 mM Tris-HCl pH8.0, 1 mM EDTA, 50 mM NaCl, and 1 mM phenyl methyl sulfonyl fluoride (PMSF). The resuspended cells were sonicated on ice with the medium tip of a Branson sonifier at setting 5 for five 40-second intervals. Between each sonification burst the sample was placed on ice for 60 seconds. The sonicated extract was then centrifuged for 30 minutes at 34,000× g and the supernatant was then divided into 10 microliter aliquots and stored frozen at −80° C. These extracts were usually stable to several rounds of freeze-and-thaw.

(i) Pac-cleavage activity of the pcp+ packaging extract

Figure 5A:
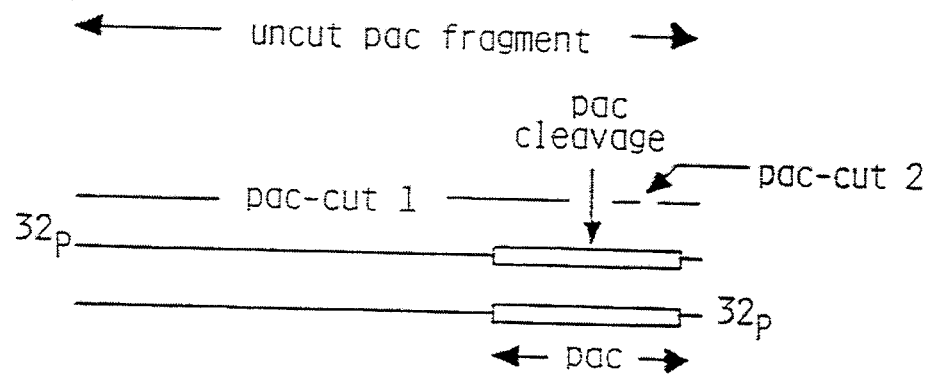
FIG. 5A illustrates that the 600 bp delta-3 pac fragment was labeled at both ends with gamma$^{32}$P-dATP.
Figure 5B:
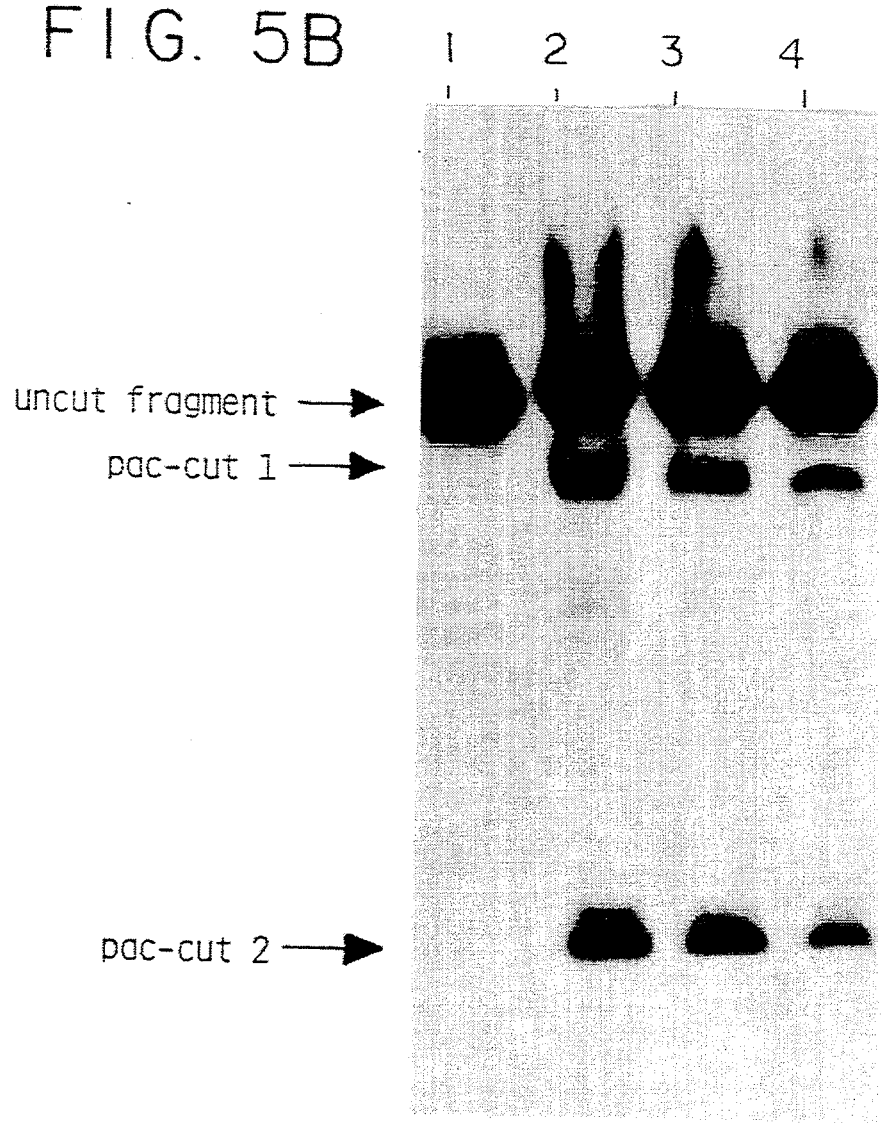
FIG. 5B illustrates the pac-cleavage activity of the pcp+ packaging extracts.

To measure pac cleavage, the 600 bp delta-3 pac fragment was used, which contained the pac site at its right end (FIG. 5A; Sternberg and Coulby, J. Mol. Biol. 194, 469–479 (1987)). The fragment was labelled at both ends with gamma$^{32}$P-dATP by using polynucleotide kinase and then incubated with various aliquots of the pcp+ extract. The reaction was carried out in 15 microliters of 10 mM Tris-HCl, pH 8.0, 50 mM NaCl, 10 mM MgCl$_2$, 1 mM DTT, 1 mM ATP, 10 micrograms sonicated calf thymus DNA with 1 microliter of labelled pac fragment (12 micrograms/ml) and either no extract or 0.01 to 1 microliter of the pcp+ extract (3.4 milligrams protein/ml). The reaction mixture was incubated for 15 minutes at 30° C. and the reaction stopped by adding SDS to a concentration of 0.2% and heating the mixture at 70° C. for 5 minutes. The products of the reaction were analyzed by polyacrylamide gel electrophoresis. Samples were loaded into the slots of a vertical 5% gel and electrophoresed for 4 hours at 150 volts. The gel was then dried and exposed to Kodak XRP film overnight. The results, illustrated in FIG. 5B, show that 1 microliter of the extract (lane 2) cleaved about 20% of the fragment, generating two new fragments not seen in the lane without added extract (lane 1). A ten-fold dilution of the extract (lane 3) reduced the amount of cleaved fragment only marginally, but an additional ten-fold dilution of extract (lane 4) reduced the efficiency of cutting to about 5%.

(b) Preparation of the 9.16 or head-tail proficient (htp+) extract

One liter of L broth was inoculated with a colony of strain NS2961 bacteria and the culture grown and induced as described above in (a) . After shifting the temperature to 42° C. and incubating the culture at that temperature for 15 minutes, the temperature was shifted back to 38° C. followed by an incubation period of 45 minutes. The culture was divided in half and the cells pelleted as described above in (a). Bacterial cells from one-half of the culture were resuspended in 1 ml of a buffer containing 20 mM Tris-HCl, pH 8.0, 50 mM NaCl, 1 mM EDTA, 5 mM MgCl$_2$, 1 mM PMSF, and 5 mM beta-mercaptoethanol and sonicated as described above in (a). Aliquots of 100 microliters were directly frozen at −80° C. Cells from the other half of the culture were resuspended in 1 ml of a solution of 50 mM Tris-HCl buffer at pH 7.4, 10% sucrose and were then frozen and thawed twice. Freezing was carried out in liquid nitrogen and the frozen cells were thawed at room temperature. An 8 micromolar solution of egg white lysozyme (10 milligrams/ml) was then added to the thawed cells and after 15 minutes at 4° C., 200 microliters of the buffer used for the sonicated htp+ extract was added. After all of the components were gently mixed at 4° C. for 5 minutes, 100 microliter aliquots of the extract were frozen at −80° C.

It should be noted that bacterial strain NS2962 was induced for a much longer period of time than was strain NS2961 before the cells were harvested. This was so because the 10.1 amber mutation in the former strain inhibited cell lysis much more dramatically than did the cm-2 mutation which was present in both cell lines. Thus, the induced NS2962 lysogen did not lyse for as long as 4 hours after induction while the induced NS2961 lysogen began to lyse about 80–100 minutes after induction. Indeed, care was taken to rapidly cool the induced NS2961 cells before they were pelleted by centrifugation to avoid lysing the cells during the centrifugation step.

(c) Preparation of the head-tail proficient extract from bacterial strain NS3210

The extract preparation procedure with this strain was modified because it did not contain the cm-2 mutation. A culture of NS3210 lyses about 50–60 minutes after induction. Thus, it must be processed more rapidly than induced cultures of NS2961 or NS3205 to obtain a functional head-tail proficient extract. A liter of induced cells was processed as in the previous section except in order to avoid cell lysis during the centrifugation step that is used to concentrate the cells, one fifth volume of a cold 50% sucrose solution was added to the culture before the centrifugation step to stabilize the cells during centrifugation. The cells were resuspended in 1 ml 50 mM Tris-HCl, pH 7.4, 10% sucrose and 40 μl aliquots distributed into 1.5 ml conical eppendorf centrifuge tubes containing 4 μl of a 10 mg/ml solution of lysozyme. The contents of the tubes were rapidly frozen in liquid nitrogen and stored at −80° C. The head-tail extract prepared from NS3210 did not contain cm-2 mutation and, thus, contained the normal ratio of phage large heads to small heads of about 10:1. This is the preferred protocol for preparing the head-tail extract.

Figure 6A:
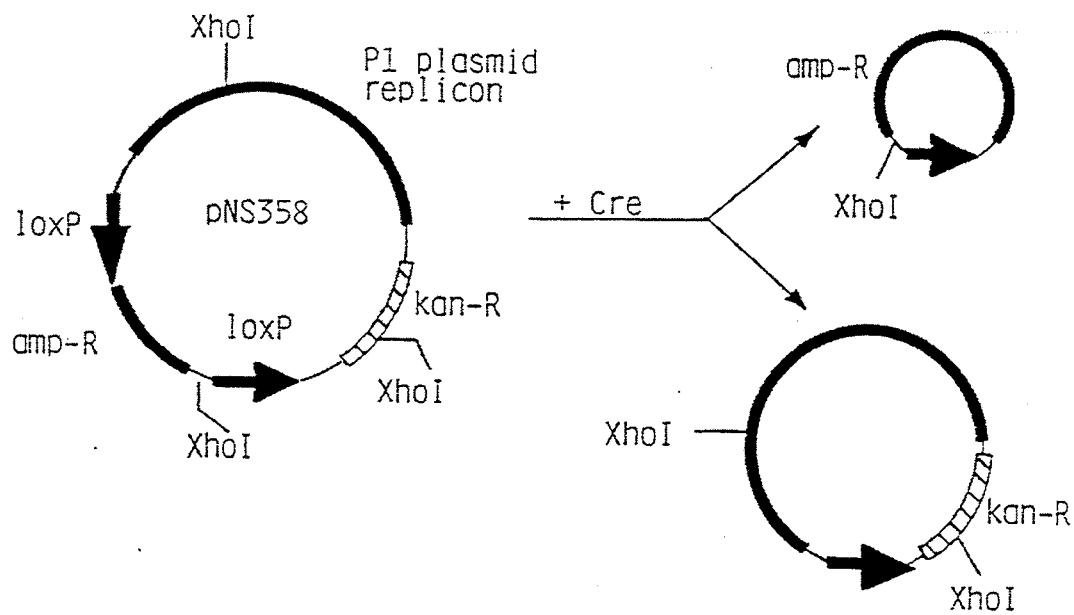
FIG. 6A illustrates the dissociation of the DNA of pNS358 when acted on by Cre recombinase.

Demonstration that Vector DNA is Acted on by Cre in Transformed BS591 Bacteria In order to demonstrate that the vectors constructed here would be processed as expected when introduced into cells containing the Cre recombinase, pNS20 and pNS358 were introduced into *E. coli* strains DH5 and BS591. DH5 did not contain a functional cre gene whereas BS591 did contain a functional cre gene. The results of transformation to amp-R and kan-R are shown in Table 2 and indicate that Cre efficiently dissociated the two domains of both of these plasmids in cells and that each domain must contain a replicon if it was to be recovered. (See FIG. 6A.)

TABLE 2

| | | Strain transformed | | | |
|---|---|---|---|---|---|
| | Replicon in | BS591 (cre+) | | DH5 (cre−) | |
| Plasmid | kan-R domain | amp | kan | amp | kan |
| pNS20 | None | 1.4 | 0.002 | 1.2 | 1.0 |
| pNS358 | P1 plasmid | 0.6 | 0.5 | 0.4 | 0.5 |

When strain BS591 was transformed with pNS20, which carried a replicon only in the amp-R domain, the efficiency of amp-R transformation was about 1000 times higher than was the efficiency of kan-R transformation. The results of transformation of strain DH5 support the conclusion that this was due to the separation of the two domains by Cre-mediated recombination between loxP sites. In this case, the efficiency of amp-R and kan-R transformation with pNS20 was the same. If the kan-R domain carried a replicon, as was the case for plasmid pNS358, then both kan-R and amp-R genes are equally represented among the transformants of strain BS591. Moreover, about 20–30% of the kan-R transformants of BS591 were ampicillin sensitive and an equal number of the amp-R transformants were kanamycin sensitive. As expected, all the transformants of DH5 (Cre−) by pNS358 DNA were both amp-R and kan-R. One unit of transformation in these experiments was meant to represent $10^6$ transformants per microgram of DNA used.

Figure 6B:
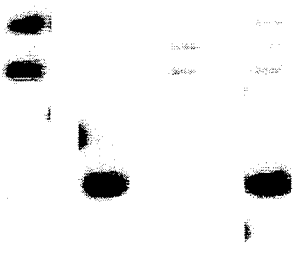
FIG. 6B illustrates that vector DNA is acted on by Cre in transformed BS591 bacteria.

Physical evidence for the dissociation of the DNA of pNS358 in BS591 (FIG. 6B) came from the restriction analysis of rapid plasmid preparation of DNA derived from the transformants of BS591 and DH5. All DNAs were digested with the restriction enzyme XhoI and the number of fragments resulting were determined by agarose gel electrophoresis and Southern hybridization. Plasmid DNA derived from the amp-R kan-R transformants of DH5 (lane 1) was indistinguishable from the original pNS358 plasmid. They both contained the expected 3 XhoI fragments. In contrast, plasmid DNA from amp-R, kan-S transformants of BS591 contained DNA with only a single XhoI site (lane 2) while plasmid DNA from kan-R, amp-S transformants of BS591 contained two XhoI fragments (lane 3). Plasmid DNA from amp-R kan-R transformants (lane 4) of BS591 contained all three species of DNA, i.e., that like pNS358, amp-R domain plasmid DNA with a single XhoI site, and kan-R domain plasmid DNA with two XhoI sites. As expected, plasmid DNA with just the kan-R domain of pNS358 was recovered in much smaller amounts (i.e., the DNA bands were much lighter) than was either pNS358 DNA or amp-R plasmid DNA. The P1 plasmid replicon in the kan-R domain replicated DNA to a much lower copy number than did the pBR322 replicon in the amp-R domain.

Demonstration of DNA packaging by pcp+ and htp+ extracts The packaging of ligated vector (pNS358) DNA Five micrograms of BamHI-digested pNS358 DNA (100 micrograms/ml) was ligated overnight to generate concatamers that ranged in size from 50 kb to 150 kb. Thirty ng of this DNA was incubated with 0.2 microliter of the pcp+ extract as described in the previous section except that the incubation period was for 60 minutes, not 15 minutes. At the end of the incubation period, 2 microliters of a buffer containing 6 mM Tris-HCl, pH 7.4, 15 mM ATP, 16 mM $MgCl_2$, 60 mM spermidine, 60 mM putrescine and 30 mM beta-mercaptoethanol was added to the reaction along with 8 microliters of the freeze-thawed htp+ extract. The resulting mixture was incubated an additional 60 minutes at 30° C. At the end of this period, the reaction was diluted to 150 microliters with TMG (10 mM Tris-HCl, pH 7.5, 10 mM $MgSO_4$, 0.1% gelatin) and DNaseI was added to a concentration of 10 micrograms/ml to destroy all of the unpackaged DNA. Five microliters of the above packaging reaction was added to $10^8$ bacterial cells of strain BS591 and the resulting mixture was incubated for a period of 10 minutes at 30° C. to allow phage adsorption to occur. The resulting infected cells were diluted with L Broth to 2 ml and grown for 1 hour at 37° C., pelleted by centrifugation, and then spread on L-amp agar plates. After overnight incubation, the plates contained 2208 colonies. This corresponded to an efficiency of packaging of $2 \times 10^6$ packaged DNA molecules/microgram of added vector DNA. If the bacterial strain used to assay the packaged vector was DH5 (Cre−), then the number of amp-R colonies detected decreased about 40-fold, indicating that Cre-mediated recombination between loxP sites was needed to cyclize the injected linear DNA. If either of the two extracts was left out of the packaging reaction, then no amp-R colonies were detected, indicating that both extracts were needed for packaging. If the sonicated htp+ extract was used instead of the freeze-thawed htp+, the packaging efficiency was unaltered. However, as the sonicated extract proved to be much less stable than the freeze-thawed extract, all subsequent experiments employed the freeze-thawed extract. Finally, analysis of the amp-R colonies indicated that 50% (25/50) were also kan-R, indicating that frequently both antibiotic resistance domains of pNS358 were packaged.

Infection of Bacteria with Vectors

One hundred microliters of an overnight culture of bacteria (2–3×10⁹ cells/ml) were incubated with an aliquot of a phage lysate or an in vitro packaging reaction at 30° C. for 10 minutes. If phage were to be assayed, 3.0 ml of molten L-top agar (0.7% agar) at 55° C. was added to the infected cells and the mixture spread on an L-agar plate. After the top agar was allowed to solidify for 5 minutes at room temperature, the plates were incubated for 16 hours at 37° C. and plaques were scored. If antibiotic-resistant cells were to be assayed, the infected cells were spread on antibiotic-containing L-agar plates and these plates were incubated for 16 hours at 37° C.

Recovery of Exogenous DNA Fragments cloned into pNS358 DNA Following In Vitro Packaging and Transformation of Cre+ Cells Plasmid with cloned inserts of *E. coli* DNA was recovered in two ways: (1) Plasmid DNA was isolated from 1 liter of cells grown overnight to 2–3×10⁹ cells/ml by the alkali lysis protocol of Birnboim et al., Nucl. Acids Res. 7, 1513–1523 (1979) and by cesium chloride ethidium bromide equilibrium centrifugation, which was described by Maniatis et al., Molecular Cloning: A Laboratory Manual (Cold Spring Harbor Laboratory, Box 100, Cold Spring Harbor, N.Y., 1982). After the DNA was removed from the gradient, it was extracted four times with cesium chloride-saturated isopropanol, dialyzed against 1 liter of a 10 mM Tris-HCl, pH 8.0, 1 mM EDTA solution for 5 hours at 4° C., extracted twice with phenol, and then precipitated with 2 volumes of ethanol in 1M LiCl₂. (2) The plasmid with cloned insert DNA was recovered from transformed cells in phage particles by infecting those cells with P1 phage. The infecting P1 DNA recombined with the resident plasmid in the cell by a Cre-mediated recombination process involving loxP sites on both DNAs. This event placed a P1 pac site adjacent to the cloned insert-plasmid and thereby permitted its packaging into phage particles. One hundred microliters of an overnight culture of transformed cells (about 2×10⁸ cells) were incubated with 6×10⁸ P1 phage for 10 minutes at 30° C. and were then diluted to 5 ml with L-Broth. The infected cells were vigorously shaken at 37° C. until cell lysis was observed (about 90 minutes). The number of phage containing the cloned fragment along with the kan-R domain of pNS358 was assessed by infecting BS591 with an aliquot of the lysate and then measuring the number of kan-R cells produced. Plaque-forming phage in the lysate were measured as previously described. Usually, the ratio of kan-R phage to plaque forming phage in these lysates was about 0.1–1%.

Amplification of a Plasmid Containing a Kan-R Gene, a P1 Plasmid Replicon, and a P1 Lytic Replicon, pNS364

Figure 7A:
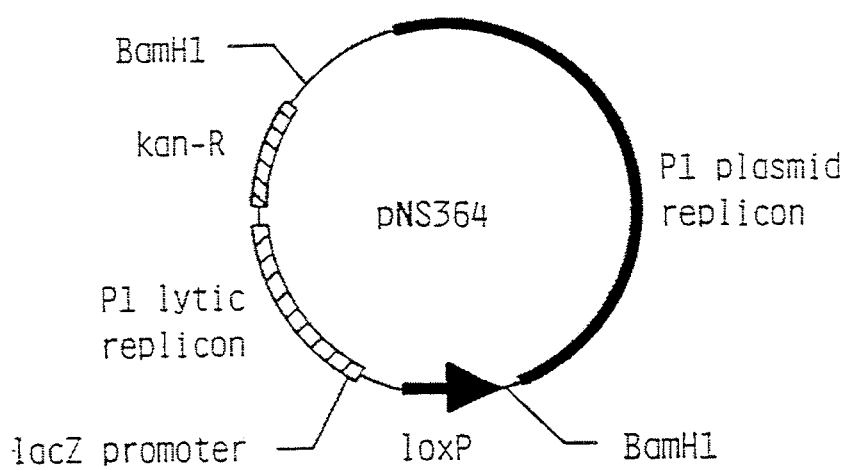
FIG. 7A shows the structure of pNS364.
Figure 7B:
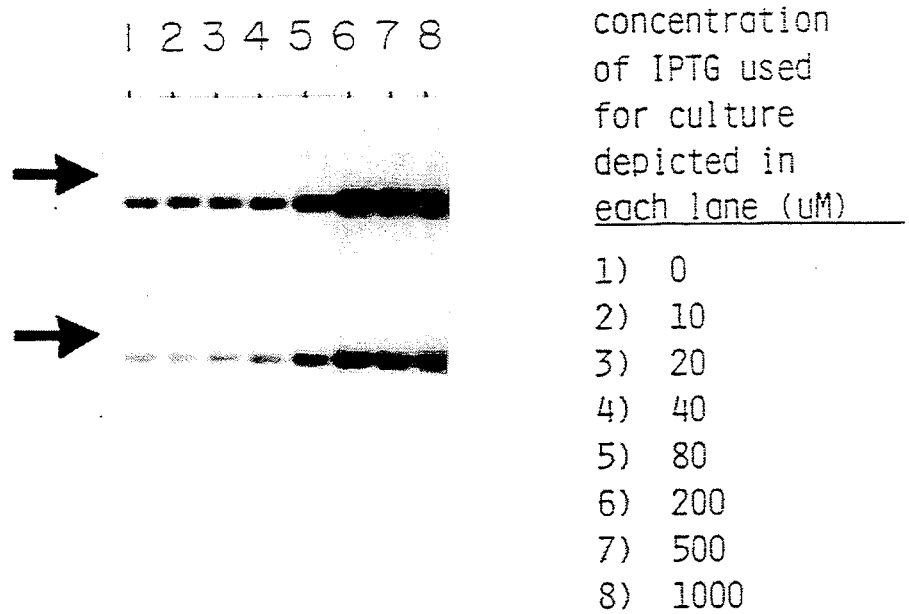
FIG. 7B illustrates amplification of plasmid pNS364 containing kan-R gene, a P1 plasmid replicon, and a P1 lytic replicon.

The structure of this plasmid is illustrated in FIG. 7A. We used it here to illustrate that a cloned multicopy replicon such as the P1 lytic replicon that is regulated by the lac gene promoter can be used to easily amplify the number of plasmid copies in the cell. Strain JM109 (lacI$^q$) was transformed with pNS364 DNA and the transformed cells were grown in L-broth. Under these conditions, the plasmid was expected to be maintained by the plasmid replicon at one copy per cell chromosome. When IPTG was added to the media, the lacI$^q$ repressor was inactivated, thus, activating the lac promoter and the P1 lytic replicon. Sixty ml of a culture of JM109 (pNS364) was grown to a density of 5×10⁷ cells/ml in L-broth at 37° C. and then divided into 8 aliquots of 5 ml each. One aliquot was grown for an additional 3 hours at 37° C. in L-broth, while each of the other seven aliquots was grown in L-broth for 3 hours with IPTG, ranging in concentration from 10 micromolar to 1 mM. Total cellular DNA was isolated from each of the cultures, digested with the restriction enzyme BamHI (which cleaved pNS364 into two fragments), and analyzed by Southern hybridization. The results (FIG. 6B) indicated that as the concentration of IPTG in the media increased, so did the plasmid copy number. At 1 mM IPTG, the copy number of the plasmid was 30–40 higher than was the copy number of the plasmid in media lacking IPTG (compare lanes 1 and 8).

EXAMPLE 1

Inserting Fragments of *E. Coli* DNA into pNS358, Packaging the Chimeric Vector DNA, Transforming Bacteria with the Packaged Chimeric Vector, Selecting Transformed Bacteria and Recovering the Inserted DNA Fragments Two micrograms of pNS358 DNA was digested with either BamHI or NotI restriction enzymes. Each of these enzymes cleaved the vector DNA once in the polylinker cloning site. The cleaved DNAs were then treated with alkaline phosphatase to prevent religation of the cleaved ends in the subsequent ligation reaction. The source of insert DNA was *E. coli* strain W3350 and the isolated DNA was greater than 200 kb in size. Prior to inserting any of the DNA in the vector, it was digested with either Sau3aI to an average size of 20–50 kb or to completion with restriction enzyme NotI. Approximately equal amounts (200 ng) of the vector DNA and *E. coli* DNAs (BamHI-digested vector with Sau3aI-digested *E. coli* DNA or NotI-digested vector and NotI-digested *E. coli* DNA) were mixed in a volume of 20 microliters and ligated overnight. One microliter of this ligation mix was packaged as described in the previous section entitled "Demonstration of DNA packaging by pcp+ and htp+ extracts" and used to transform *E coli* strain BS591 by infection as described in the section "Infection of bacteria with vectors". The resulting transformed bacteria were detected as kan-R colonies as shown in Table 3.

TABLE 3

| In Vitro Packaging of pNS358 - *E. coli* DNA | | |
|---|---|---|
| DNA added to the in vitro packaging reaction | Kanamycin-Resistant Colonies per ug vector DNA | |
| | BS591 | DH5 (cre⁻) |
| 1. Sau3aI inserts | | |
| pNS358 - BamHI | <10⁴ | |
| pNS358 - BamHI + ligase | 2 × 10⁶ | 2.4 × 10⁴ |
| pNS358 - BamHI-AP + ligase | 2 × 10⁴ | |
| pNS358 - BamHI-AP + + ligase | 4 × 10⁵ | 6.0 × 10³ |
| *E. coli* DNA-Sau3aI | | |
| 2. NotI inserts | | |
| pNS358 - NotI | <10⁴ | |
| pNS358 - NotI + ligase | 2 × 10⁶ | 4.2 × 10⁴ |
| pNS358 - NotI-AP + ligase | 1 × 10⁴ | |

TABLE 3-continued

In Vitro Packaging of pNS358 - E. coli DNA

| DNA added to the in vitro packaging reaction | Kanamycin-Resistant Colonies per ug vector DNA | |
|---|---|---|
| | BS591 | DH5 (cre−) |
| pNS358 - NotI-AP + + ligase E. coli DNA-NotI | $1.8 \times 10^5$ | $8.0 \times 10^3$ |

AP = Alkaline phosphatase treated DNA fragments

The efficiency of packaging BamHI or NotI-digested vector DNA that had not been treated with alkaline phosphatase was about $2 \times 10^6$ packaged DNA molecules/microgram of added vector DNA. Treatment of the vector DNA with alkaline phosphatase reduced the recovery of DNA after packaging about 100 to 200-fold, but Sau3aI- or NotI-digested E. coli DNA may be added to the ligation reaction to partially restore that loss. The interpretation of these results was that the phosphatase-treated vector DNA cannot be ligated to large concatamers and consequently cannot be packaged efficiently. Adding E. coli DNA inserts to the vector DNA permitted it to reach a size that can be packaged. Depending on the particular packaging reaction, 50–90% of kan-R colonies were amp-S, indicating that they lacked the amp-R domain of pNS358.

Recovery and Characterization of the Packaged pNS358 DNA and the E. Coli Inserts it Contained (a) The Sau3aI Clones The plasmid DNA in each of the cultures grown from the 10 separate colonies generated by packaging the Sau3aI-digested E. coli DNA inserted in pNS358 was isolated by the alkali procedure of Birnboim et al., Nucl. Acids Res. 7, 1513–1523 (1979), and analyzed by restriction enzyme digestion. The DNA of two of the plasmids was identical to the kan-R domain of pNS358 DNA, but the rest contained substantially more DNA than was present in the vector, including many new restriction fragments. Digests of the vector (lane 3) and of five of the vector-Sau3aI chimeras (lanes 4–8) with the restriction enzymes BglII, XhoI, PvUII and ECOV are shown in FIG. 8A. It appeared that new DNA fragments seen in lanes 4–8 come from the insertion of E. coli Sau3aI fragments. Lanes 1 and 2 of FIG. 8A contained DNA size markers. The biggest plasmid isolated was 38–40 kb. Pulse field gel analysis indicated that it contained two NotI fragments of 22 kb and 17 kb (FIG. 8B, lane 3). Lane 1 contained packaged vector DNA and lane 2 contained a second Sau3aI-chimera digested with NotI. These results suggest that most, if not all of the Sau3aI inserts were packaged in small-headed (P1S) particles, whose capacity is no greater than 40 kb.

(b) The NotI clones

The recent NotI restriction map of E. coli DNA described by Smith et al., Science 236, 1448–1453 (1987), shows that NotI digestion of E. coli DNA produces five DNA fragments that can be packaged by the in vitro P1 packaging system of this invention. These fragments are 20 kb, 40 kb, 43 kb (two fragments of this size), and 95 kb in size. After inserting NotI fragments into pNS358 DNA and cloning them in BS591 bacteria as described for Sau3aI inserts, the plasmid DNA from 5 clones was examined. The DNA of two of the cloned plasmids contained only the kan-R domain of pNS358. When the DNA from the other three cloned plasmids were digested with NotI, they were shown to carry NotI fragments greater than 30 kb in size in addition to the kan-R domain of the vector. The size of the NOtI inserts in these DNAs was more precisely determined by pulse gel electrophoresis. One of the plasmids (FIG. 8B, lane 11) contained a NotI insert that migrated with a 40 kb marker in the gel, while the other two (FIG. 8B, lanes 9 and 10) contained inserts that migrate slightly above a 42.5 kb marker. All three clones contained a 12 kb NotI fragment that corresponded to the kan-R domain of the vector. The DNA of one of the clones containing a 43 kb insert (lane 10) also contained a 6 kb NotI fragment, whose origin was unclear as no such E. coli fragment has been described. Digestion of the plasmid DNA shown in lane 10 with BglII and XhoI rather than with NotI produced a family of fragments whose total size exceeds 60 kb, confirming the size estimate based on the NotI digest (FIG. 8C, lane 2). Based on their large size, the three plasmids with NotI inserts must have been packaged by the large P1 (P1B) heads.

Figure 9A:
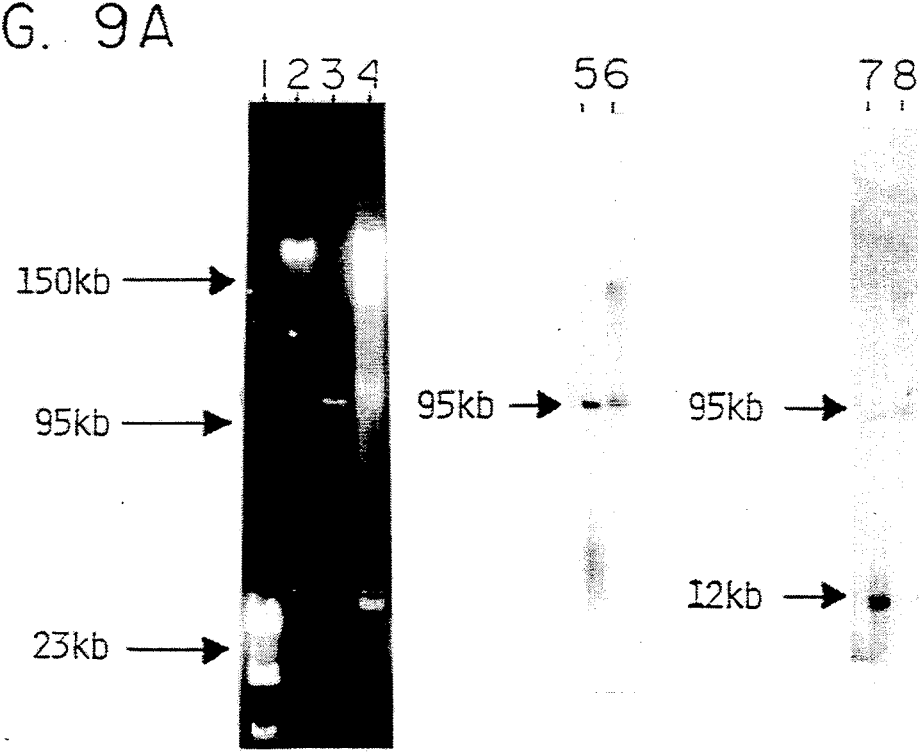
Figure 9B:

The genes of the E. coli tryptophan biosynthesis operon are present on a 95 kb NotI fragment of E. coli DNA and were utilized to show that a fragment of that size could be packaged into P1 heads in vitro. Phage resulting from the packaging reaction using NotI digested E. coli DNA were used to infect the trp− strain NS3067 of E. coli containing a lambda-P1:cre prophage. The resulting kan-R bacteria were isolated and tested to determine if they could grow on minimal agar in the absence of tryptophan. Two of 50 tested grew. The plasmid DNA was isolated from one of the positive clones and shown by ethidium bromide staining (FIG. 9A, lanes 3–4) or by Southern analysis of pulse field gels (FIG. 9A, lanes 5–6) to contain a 95 kb E. coli NotI fragment that hybridized to an E. coli trpE gene probe. Lanes 3 and 5 contained the plasmid DNA digested by NotI and lanes 4 and 6 contained E. coli DNA digested with NotI. When the pulse field gel was probed with kan-R gene DNA, a 12 kb DNA fragment appeared in the lane (lane 7) containing the trp plasmid DNA, but not in the lane (lane 8) containing E. coli DNA. That fragment corresponded to the kan-R domain of pNS358 DNA. Digestion of the trp plasmid and E. coli DNA (FIG. 9B) with a variety of restriction enzymes (BglII-XhoI, lanes 1 and 2, HindIII, lanes 3 and 4, SmaI, lanes 5 and 6) followed by Southern analysis using the trp plasmid DNA as a probe, indicated that the plasmid DNA contained many fragments that were identical in size to bonafide E. coli DNA fragments. Lanes 1, 3, and 5 contained E. coli DNA, and lanes 2, 4, and 6 contained trp plasmid DNA. Where fragments were present in the E. coli lanes and not in the plasmid lanes, or vice versa, this indicates either that they were derived from the vector or that they represented a junction between vector and E. coli DNA. Taken together, these results indicated that the P1 packaging system can accommodate as much as 107 kb of DNA (the 95 kb NotI insert plus the 12 kb plasmid kan-R domain) and that the vector faithfully replicated that DNA as an extrachromosomal plasmid.

EXAMPLE 2

Use of the pNS358-lyt Vector to Amplify Cloned DNA Fragments

Two micrograms of pNS358-lyt DNA was digested with BamHI or NotI and used to clone Sau3aI and NotI fragments of E. coli DNA, respectively, as described in Example 1. Following in vitro packaging of the vector DNA with the Sau3aI or NotI fragment inserts as in Example 1, the packaged chimeric DNA was injected into strain NS2974 and kan-R transformants were selected. The DNA of individual kan-R transformants was isolated as described in Example 1 and in the section "Recovery of exogenous DNA fragments cloned into pNS358 DNA following in vitro packaging and transformation of Cre+ cells" (pp. 27-28), and was shown to contain *E. coli* DNA inserts by restriction enzyme digestion and Southern hybridization analysis. To determine if the vector-insert DNA can be amplified by the lytic replicon in the vector, a culture of strain NS2974 bacteria containing a chimeric plasmid was divided in half and grown for 3 hours in either the presence or absence of 1 mM IPTG. At the end of the growth period, total cellular DNA was isolated from each of the two cultures and plasmid copy number measured by Southern hybridization as described for plasmid pNS364 in the section entitled "Amplification of plasmid containing a kan-R gene, a P1 plasmid replicon, and a P1 lytic replicon, pNS364". DNA from the culture grown with IPTG contained 20-30 times more vector insert plasmid DNA than does the DNA isolated from the culture grown without IPTG. This result was confirmed by isolating supercoiled circular DNA from the two cultures using CsCl-ethidium bromide equilibrium density gradients.

EXAMPLE 3

Effects of the *Escherichia Coli* mcrAB Restriction System on the Cloning of Size-Selected Sau3AI hyman DNA fragments To determine whether the elements of the P1 cloning system (pNS582, NS2961, NS2962, and BS591) used to clone *Escherichia coli* DNA fragments could be used to clone efficiently high molecular weight size-selected DNA fragments from a mammalian DNA source, the DNA fragments shown in FIG. 10 were ligated to BamHI-digested alkaline-phosphatase treated pNS582tet14 DNA. pNS582tet14 DNA was used here rather than pNS582 DNA because it simplified the analysis of the cloning process. Rather than determining whether a particular transformant contained an insert by isolating and digesting plasmid DNA, with pNS582tet14 DNA as a vector, the fraction of transformants with inserts was simply assessed by determining the fraction of kan-R cells that were tet-S. An experiment similar to that described in Table 3 was performed except the size selected human DNA was used rather than the *Escherichia coli* DNA. Less than 2% of the kan-R transformants were tet-S. It appeared that the low cloning efficiency of the human DNA when compared to that of the bacterial DNA was due to restriction by the bacterial mcrAB system. As shown by Woodcock et al., Nucl. Acids. Res. 16, pp 4465-4482 (1988) and Raleigh et al., Nucl. Acids. Res. 16, pp 1563-1575 (1988), the mcrAB system recognizes DNA containing methyl CpG ($^{Me}$CpG) as foreign and degrades it. Since the CpG base pair in mammalian and plant DNA frequently contains methyl cytosine, that methylated DNA will be digested in an mcrA+ mcrB+ recipient bacterial strain (such as BS591) before it is recovered. Moreover, the human DNA fragments that will be recovered will likely be highly biased for DNA sequences in which $^{Me}$CpG is under-represented. To deal with this issue, the recipient strain BS591 was replaced with NS3145. Like BS591, strain NS3145 contains a constitutively expressed P1 cre recombinase gene for the cyclization of the injected linear vector DNA, but unlike BS591, it is mcrA− and mcrB−. NS3145 also contains an F′lacI$^q$ plasmid that inhibits the P1 lytic replicon in the vector until IPTG is added (see Example 2). When NS3145 was used instead of BS591, the frequency of transformants increased from <2% to about 20-30%. Still this frequency was significantly lower than that obtained when bacterial DNA fragments were cloned. This observation could be explained if degradation of $^{Me}$CpG-containing DNA was occurring not only in the mcrA+, mcrB+ recipient cell line but also in packaging extracts prepared from mcrA+, mcrB+ bacteria, such as NS2961 and NS2962. Bacterial strains similar to NS2961 and NS2962 (NS3205 and NS3208, respectively) were constructed except that they contained mcrA− and mcrB− and recD− mutations. The recD gene produces a major nuclease of *Escherichia coli*, Exonuclease V. When packaging extracts prepared from NS3205 and NS3208 were used to package ligation reactions like those described in Table 3 containing BamHI-digested pNS582tet14 DNA and size selected Sau3AI-digested human DNA fragments, and the resulting transformants recovered in NS3145, as much as 60-80% of the kan-R transformants were tet-S. In contrast, if the bacterial strains used to prepare the packaging extracts were recD− but mcrA+ and mcrB+, tet-S transformants were recovered with no higher efficiency (20-30%) than they were with NS2961 and NS2962 extracts. It was concluded from these studies that the mcrAB system which was present in both the packaging extracts and in the Cre+ recipient bacterial strain interfered with the cloning of human DNA fragments by degrading the DNA fragments.

EXAMPLE 4

Increasing the Size of Human DNA Fragments Recovered by the P1 Cloning System

Figure 11:
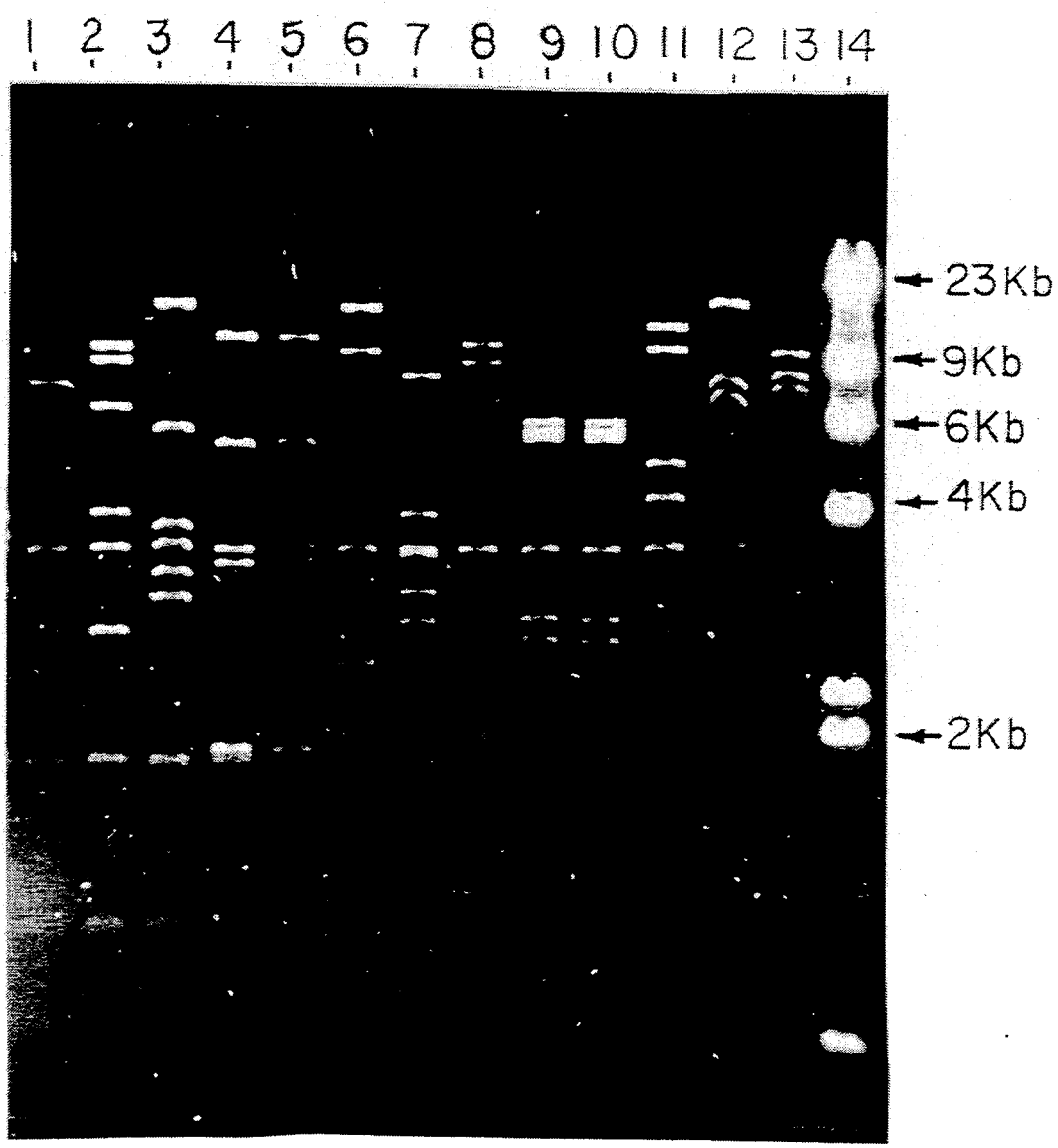
FIG. 11 illustrates recovery and characterization of the packaged pNS582tet14 DNA and human DNA inserts it contained.

While the use of mcrA−, mcrB− bacterial strains, to prepare packaging extracts and the recipient bacterial strains into which the packaged DNA was injected, resulted in the production of a high percentage of kan-R transformants that contained cloned human DNA fragments, analysis of the plasmid DNA in those transformants indicated that many of the transformants contained cloned human fragments that were smaller than expected based on the size of the starting population of DNA. For example, in an experiment in which the starting population of fragments was about 30 kb to 80 kb in size, most of the plasmids recovered contained cloned fragments in the 30-40 kb range. FIG. 11 shows the results for plasmid DNAs isolated from 12 kan-R, tet-S transformants. Those DNAs (lanes 2-13) were analyzed by agarose gel electrophoresis after being digested by restriction enzymes BglII and XhoI. Using phage lambda DNA size standards (lane 14) the amount of human DNA in any plasmid can be determined by summing the size of all of the fragments in any one lane and then subtracting the size of the kan-R domain of the pNS582tet14 vector DNA (about 15 kb). Based on such an analysis, only 3 of 48 plasmids examined had inserts larger than 50 kb. Lane 1 of FIG. 11 contained a BglII-XhoI digest of a plasmid containing just the kan-R domain of pNS582.

It was believed that the larger human fragments were being excluded from the recovered clones for two reasons: 1) The ratio of large to small P1 heads was 1:1 in the head-tail proficient extract used in these experiments. This low ratio of large to small heads (under normal conditions it is 10:1) was due to the cm-$^2$ mutation present in strain NS3205. Presumably, the reduced fraction of large heads in this extract reduced the recovery of vector with larger cloned fragments. Moreover, this effect was probably exacerbated because smaller DNA fragments in any fragment population are more likely to be cloned as they are less subject to breakage than are the larger fragments. 2) A second possible reason for the preferential recovery of small cloned fragments derives from the nature of the ligation reactions that produce the substrate for P1 headful packaging and from the nature of headful packaging process itself as is discussed below. Thus, ligation reactions need to be carried out in large vector DNA excess to insure that the fragments to be cloned ligate to vector DNA rather than to other fragments. If the latter were to occur, DNA segments that come from different parts of the genome that is being cloned would become linked, a circumstance that would generate incorrect genomic maps. If ligation reactions are carried out in large vector excess at relatively high DNA concentrations (>10 μg/ml) concatemers are produced consisting of alternating vector and insert DNA. An example of such a concatemer produced when BamHI-digested, alkaline phosphatase treated pNS582tet14 DNA is ligated to Sau3AI-digested human DNA is shown in FIG. 12A. When this concatemer is packaged by the P1 headful packaging system, packaging is initiated from a pac site in one of the vector molecules and is not completed until a headful of DNA (110-115 kb) is taken into an empty P1 head. The consequence of such a packaging process is that more than one copy of vector DNA and more than one human DNA fragment may be packaged into a single phage head, especially if the fragments ligated to vector DNA are small relative to the P1 headful size (FIG. 12A). This means that the smaller human DNA fragments cannot only be packaged into small P1 heads, but also can be packaged in large P1 heads as part of a larger concatemer. When that packaged concatemer DNA is injected into strain NS3145 all DNA segments flanked by loxP sites will be cyclized and recovered. Included among these are kan-R domain plasmid molecules with no inserts, and kan-R domain plasmids with small human DNA inserts (FIG. 12A).

To overcome these problems two modifications were made to the cloning system. First, bacterial strain NS3210 was substituted for NS3205 in the preparation of the head-tail proficient extract. Since the former contained the cm mutation, it produced 5-10 times more large P1 heads than small P1 heads. The am131 mutation in NS3210 and the am9.16 mutation in NS3205 both produced a pacase defective-phenotype. A second modification in the cloning system involved changing the way the vector DNA was processed before ligating it to insert DNA. With this approach concatemers were not generated during the ligation reaction. To take advantage of this approach, the pNS582tet14 vector DNA was modified, as described above, by inserting a "stuffer" fragment of about 10 kb (10.6 kb) from Adenovirus DNA into the unique ScaI site in the amp-R domain of the vector such that the final product (pNS582tet14Ad10) had about a 10-11 kb stuffer DNA fragment inserted between the ScaI site and plasmid replicon-proximal loxP site (FIG. 4). The size of DNA to be cloned was in the 60 kb to about 90 kb range. The stuffer fragment was inserted into a site which was not recovered during cyclization. The modified ligation procedure consisted of cleaving pNS582tet14Ad10 DNA with ScaI and BamHI and treating the product with alkaline phosphatase. Two vector fragments (arms) were generated by this procedure which could ligate to the Sau3AI-digested size-selected human DNA fragments at their BamHI ends but could not ligate to any DNA in the reaction at their blunt end producing sites, the ScaI ends. The latter circumstance prevented the formation of concatemers and resulted in ligated products consisting of a human DNA fragment sandwiched between the two vector arms (FIG. 12B). The shorter vector arm contained the pac site from which packaging is initiated and both vector arms contained loxP sites. The size of insert DNA in the structure shown in FIG. 12B determined whether the insert will be recovered. If the insert is less than 70 kb in size, there is not enough DNA between pac and the end of the molecule to fill the head and packaging will abort. If the insert is greater than 95 kb then the head will be filled before the distal loxP site has been encapsidated and the packaged DNA will not be recovered because it cannot recyclize after it is injected into the recipient Cre+ bacterial strain, NS3145. The size range of DNA that is packageable with vector arms corresponded to the size of the DNA between the distal loxP site and the right end of the ligated molecule (FIG. 12B); namely, the size of the Adenovirus "stuffer" fragment.

Figure 13A:
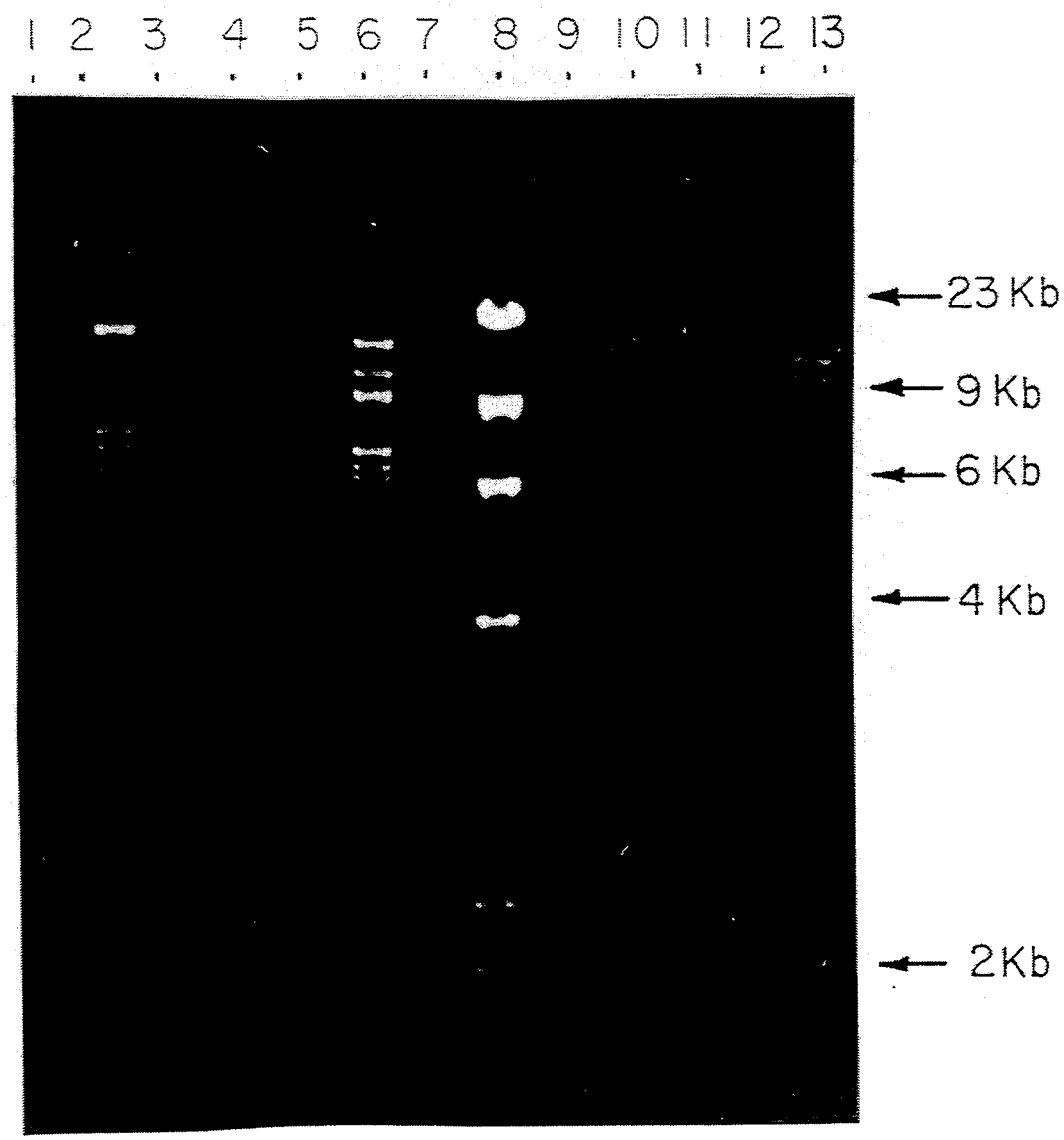
FIG. 13A illustrates recovery and characterization of packaged pNS582tet14Ad10 DNA and human inserts it contained. The DNA bands were detected by ethidium bromide staining.
Figure 13B:
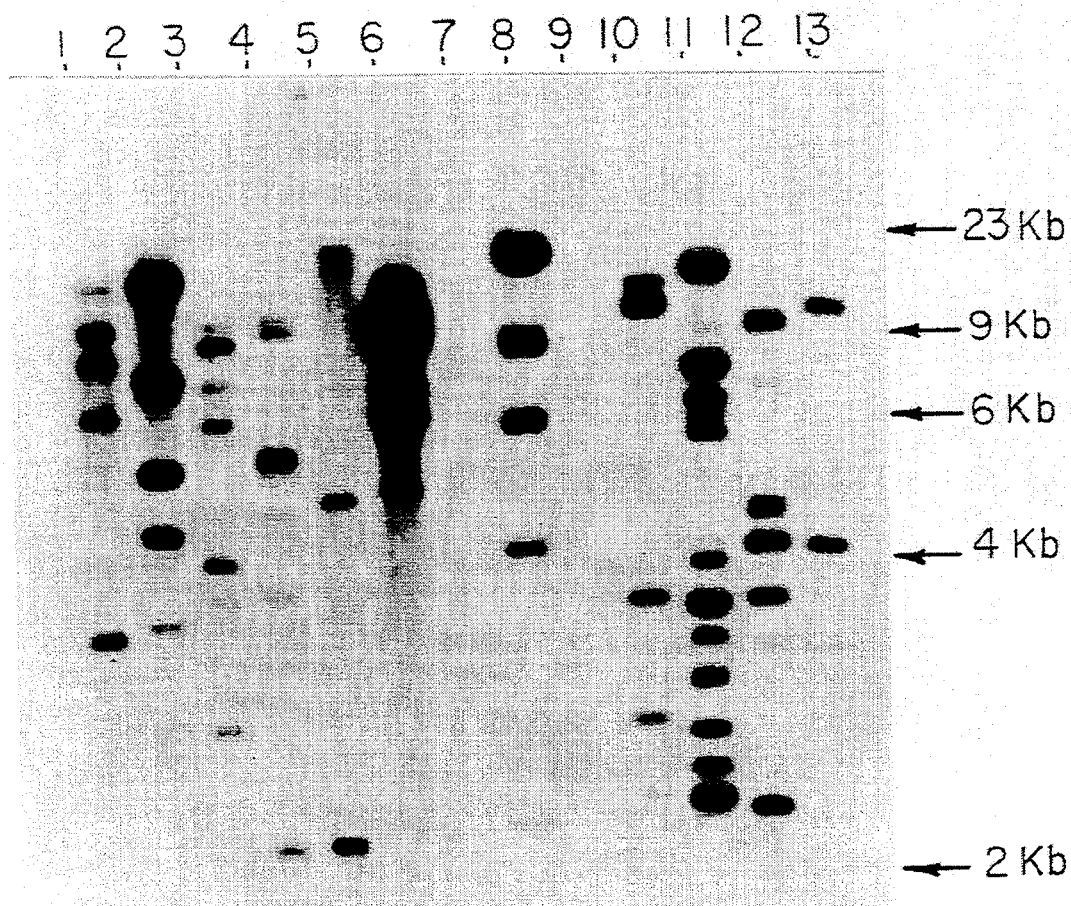
FIG. 13B is the same as 13A except bands were detected by hybridization to human genomic DNA probe.

Using extracts derived from cell lines NS3208 and NS3210, the pNS582tet14Ad10 vector, recipient strain NS3145 and size selected human DNA fragments in the 60-90 kb range (fractions 6-9, FIG. 10) kan-R transformants were generated, almost all of which (>80%), contained human DNA inserts that were in the 70-90 kb size range. FIG. 13 shows the DNA from some of the clones with inserts (lanes 1-6; 10-13) following BglII and XhoI digestion and agarose gel electrophoresis. As a control, digested kan-R domain DNA without an insert was also shown (lane 7) and a HindIII-digested k DNA marker (23 kb, 9 kb, 6 kb, 4.3 kb, 2.3 kb and 2.0 kb) (lane 8). The DNA in FIG. 13A was visualized by ethidium bromide staining and that in FIG. 13B by hybridization to a total human genomic DNA probe after Southern transfer. The latter procedure detected about $\frac{1}{2}$-$\frac{2}{3}$ of the human DNA fragments. Since fragments smaller than 70 kb were recovered in this cloning process, it would appear that the need to completely fill the P1 head is not stringent.

What is claimed is:

1. An in vitro headful packaging system for cloning foreign DNA fragments as large as 95 kb comprising:
    (a) modifying vector DNA by inserting a stuffer fragment into a blunt end producing site wherein the stuffer fragment is oriented such that the blunt end producing site is oriented in a clockwise direction with respect to a pac site;
    (b) digesting the product of step (a) to produce two vector arms each of which contains (i) a blunt end, (ii) another end which is compatible with the foreign DNA fragment which is to be cloned, and (iii) a loxP site;
    (c) ligating the foreign DNA to the product of step (b) without generating concatemers;
    (d) reacting the product of step (c) with pac cleavage proficient extract and head-tail proficient extract wherein the ratio of large heads to small heads in the head-tail extract is at least 5:1;
    (e) infecting a Cre+ bacterial strain with the product of step (d); and (f) recovering the cloned DNA.

2. A process according to claim 1 wherein the stuffer fragment has a size in the range from about 5 kb to about 20 kb.

3. A process according to claim 2 wherein the stuffer fragment is ScaI-BamHI fragment of about 10 kb from Adenovirus DNA.

4. A process according to claim 1 wherein the in vitro headful packaging system consists of (i) pac cleavage proficient extract prepared from a bacterial strain designated NS3208, and (ii) head-tail proficient extract prepared from a bacterial strain designated NS3210.

5. A process according to claim 1 wherein the Cre+ bacterial strain has a lacI$^q$ repressor.

6. A process according to claim 5 wherein the Cre+ bacterial strain is the strain designated NS3145.

7. A process according to claim 5 wherein IPTG is added after step (e) to depress the lacI$^q$ repressor.

8. A process according to claim 1 wherein the DNA to be cloned is selected to generate fragments between 60 to 95 kb in size, said selection occurring prior to step (c).

9. A process according to claim 1 wherein the product of step (e) is amplified and then recovered.

10. A vector for cloning foreign DNA fragments as large as 95 kb in an in vitro headful packaging system as defined in claim 1 wherein said vector has a pac site, a plasmid replicon, two lox P recombination sites which are oriented in the same direction, and a polylinker cloning site.

11. A vector for cloning DNA fragments comprising the following sequence: P1 loxP site-ampicillin resistance gene-pBR322 ori-pac-P1 loxP site-polylinker cloning site-kanamycin resistance gene-P1 plasmid replicon wherein said sequence is circularized such that the P1 plasmid replicon is attached to the first P1 loxP site so that the sequence reads in a counterclockwise direction.

12. A vector according to claim 11 wherein said vector has a P1 lytic replicon under control of a lac promoter inserted between the polylinker cloning site and the kanamycin resistance gene.

13. A vector for cloning DNA fragments comprising the following sequence: P1 loxP site-ampicillin resistance gene having a ScaI site-pBR322 ori-pac-P1 loxP site-tetracycline resistance gene having a BamHI site and a SalI site which replace the BamHi and SalI sites present in a polylinker cloning site-P1 lytic replicon under control of a lac promoter-kanamycin resistance gene-P1 plasmid replicon wherein said sequence is circularized such that the P1 plasmid replicon is attached to the first P1 loxP site so that the sequence reads in a counterclockwise direction.

14. A method of cloning and controlling amplification of DNA fragments as large as 95 kb in a vector containing a pac site, a plasmid replicon, two lox P recombination sites which are oriented in the same direction, a polylinker cloning site and a multicopy replicon under control of a lac promoter, said method comprising:
(a) ligating a DNA fragment to said vector DNA;
(b) reacting the product of step (a) with pac cleavage proficient extract and head-tail proficient extract;
(c) infecting a Cre+ bacterial strain having a lacI$^q$ repressor with the product of step (b);
(d) adding IPTG to culture medium; and
(e) recovering the cloned and amplified DNA.

15. A process for in vitro P1 bacteriophage packaging of the DNA of the vector of claims 11, 12, or 13 having an exogenous DNA fragment inserted therein comprising contacting the DNA of the fragment-containing vector with pac-cleavage proficient extract and head-tail proficient extract wherein said fragment has a size equal to or less than 95 kb.

16. A process according to claim 15 wherein said pac-cleavage proficient extract is prepared from the bacterial strain designated NS2962 or NS3208.

17. A process according to claim 15 wherein the head-tail proficient extract is prepared from the bacterial strain designated NS2961 or NS3210.

18. A method of cloning and controlling amplification of DNA fragments as large as 95 kb comprising:
(a) inserting an exogenous DNA fragment into the polylinker cloning site of the vector of claim 12;
(b) contacting the product of step (a) with pac-cleavage proficient extract and head-tail proficient extract;
(c) infecting a Cre+ gram-negative bacterial strain having a lacI$^q$ repressor with the product of step (b);
(d) derepressing the lacI$^q$ repressor by adding IPTG to the product of step (c); and
(e) recovering the cloned and amplified DNA.

19. A method according to claim 14 or 18 wherein the Cre+ bacterial strain is strain designated NS2974 or NS3145.

20. A method according to claim 14 or 18 wherein the pac-cleavage proficient extract is prepared from the bacterial strain designated NS2962 or NS3208.

21. A method according to claim 14 or 18 wherein the head-tail proficient extract is prepared from the bacterial strain designated NS2961 or NS3210.

22. A method of cloning DNA fragments as large as 95 kb comprising:
(a) inserting an exogenous DNA fragment into the polylinker cloning site of the vector of claim 11; (b) contacting the product of step (a) with pac-cleavage proficient extract and head-tail proficient extract;
(c) infecting a Cre+ gram-negative bacterial strain with the product of step (b); and
(d) recovering the cloned vector DNA.

23. A method according to claim 14 wherein the Cre+ strain is the bacterial strain is the strain designated BS591.

24. A vector according to claim 13 wherein a DNA stuffer fragment is cloned into the ScaI site of the ampicillin resistance gene.

25. A vector according to claim 24 wherein the DNA fragment cloned into the ScaI site has a size in the range from about 5 to about 20 kilobases.

26. A method of cloning and controlling amplification of DNA fragments comprising:
(a) inserting an exogenous DNA fragment into the vector of claims 24 or 25;
(b) contacting the product of step (a) with pac-cleavage proficient extract and head-tail proficient extract;
(c) infecting a Cre+ gram-negative bacterial strain having a lacIq$^q$ repressor with the product of step (b);
(d) derepressing the lacI$^q$ repressor by adding IPTG to the product of step (c); and
(e) recovering the cloned and amplified DNA.

27. A method according to claim 26 wherein the Cre+ bacterial strain is the strain designated NS2974 or NS3145.

28. A method according to claim 26 wherein the pac-cleavage proficient extract is prepared from the bacterial strain designated NS2962 or NS3208.

29. A method according to claim 26 wherein the head-tail proficient extract is prepared from the bacterial strain designated NS2961 or NS3210.

30. A vector according to claim 25 wherein a ScaI-BamHI fragment of about 10 kb from Adenovirus DNA is inserted into the ScaI site of the ampicillin resistance gene.

* * * * *